US008911751B2

(12) United States Patent
Touitou et al.

(10) Patent No.: US 8,911,751 B2
(45) Date of Patent: Dec. 16, 2014

(54) COMPOSITIONS FOR NASAL DELIVERY

(75) Inventors: Elka Touitou, Jerusalem (IL); Biana Godin, Jerusalem (IL); Shaher Duchi, Kfar Rama (IL)

(73) Assignee: Yissum Research Development Company of the Hebrew University of Jerusalem, Jerusalem (IL)

(*) Notice: Subject to any disclaimer, the term of this patent is extended or adjusted under 35 U.S.C. 154(b) by 777 days.

(21) Appl. No.: 12/078,317

(22) Filed: Mar. 28, 2008

(65) Prior Publication Data

US 2009/0047234 A1 Feb. 19, 2009

Related U.S. Application Data

(63) Continuation-in-part of application No. PCT/IL2006/001187, filed on Oct. 15, 2006.

(60) Provisional application No. 60/907,340, filed on Mar. 29, 2007, provisional application No. 60/724,904, filed on Oct. 11, 2005.

(51) Int. Cl.
*A61K 9/00* (2006.01)
*A61K 47/24* (2006.01)
*A61K 31/196* (2006.01)
*A61K 31/05* (2006.01)
*A61K 47/34* (2006.01)
*A61K 47/10* (2006.01)
*A61K 38/16* (2006.01)
*A61K 31/5513* (2006.01)

(52) U.S. Cl.
CPC .............. *A61K 9/0043* (2013.01); *A61K 47/24* (2013.01); *A61K 31/196* (2013.01); *A61K 31/05* (2013.01); *A61K 9/0019* (2013.01); *A61K 47/34* (2013.01); *A61K 47/10* (2013.01); *A61K 38/16* (2013.01); *A61K 31/5513* (2013.01)
USPC .......................................... 424/400

(58) Field of Classification Search
USPC .......................................... 424/400
See application file for complete search history.

(56) References Cited

U.S. PATENT DOCUMENTS 4,614,730 A 9/1986 Hansen et al.
4,746,680 A 5/1988 Jeffery et al.
(Continued)

FOREIGN PATENT DOCUMENTS

EP 0 200 444 5/1986
WO 95/35095 12/1995
(Continued)

OTHER PUBLICATIONS

A. Brossi et al., "Arteether, A New Antimalarial Drug: Synthesis and Antimalarial Properties," J. Med. Chem., 1988 31, pp. 645-650.
(Continued)

*Primary Examiner* — Trevor Love
(74) *Attorney, Agent, or Firm* — Browdy and Neimark, PLLC

(57) ABSTRACT

The present invention concerns a method of administering at least one active pharmaceutical agent to a patient in need thereof, which method comprises the intranasal administration of a composition comprising a therapeutically effective amount of this agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of said composition being not less than 30% by weight, the phospholipids forming vesicles in said composition. Further are disclosed pharmaceutical compositions and combinations suitable for intranasal delivery.

40 Claims, 16 Drawing Sheets

(56) References Cited

U.S. PATENT DOCUMENTS

| | | | |
|---|---|---|---|
| 4,929,629 | A | 5/1990 | Jeffery |
| 5,436,272 | A | 7/1995 | Scheinbaum |
| 5,540,934 | A | 7/1996 | Touitou |
| 5,711,965 | A | 1/1998 | Ghyczy et al. |
| 5,716,638 | A | 2/1998 | Touitou |
| 6,017,963 | A * | 1/2000 | Alfonso et al. ............... 514/646 |
| 6,350,458 | B1 | 2/2002 | Modi |
| 6,627,211 | B1 | 9/2003 | Choi et al. |
| 6,686,473 | B2 | 2/2004 | Lemmens et al. |
| 2002/0048551 | A1 | 4/2002 | Keller et al. |
| 2004/0204413 | A1 | 10/2004 | Faour et al. |
| 2007/0043032 | A1 | 2/2007 | Mainville |

FOREIGN PATENT DOCUMENTS

| | | |
|---|---|---|
| WO | 99/52524 | 10/1999 |
| WO | 00/01351 | 1/2000 |
| WO | 01/06987 | 2/2001 |
| WO | 03/000174 | 1/2003 |
| WO | 03/048167 | 6/2003 |
| WO | 03/080606 | 10/2003 |
| WO | 03/099293 | 12/2003 |
| WO | 2005/107467 | 11/2005 |
| WO | 2005/117830 | 12/2005 |
| WO | 2006/004749 | 1/2006 |
| WO | 2007/043057 | 4/2007 |
| WO | 2007/144085 | 12/2007 |
| WO | 2008107410 | 9/2008 |
| WO | 2008/120207 | 10/2008 |

OTHER PUBLICATIONS

J. E. Jeffery et al., "Synthesis of Sibutramine, a Novel Cyclobutylalkylamine Useful in the Treatment of Obesity, and its Major Human Metabolites," J. Chem. Soc., Perkin. Trans. 1, 1996, pp. 2583-2589.

L.H. Sternbach et al., "Quinazolines and 1,4-Benzodiazepines. 111.1 Substituted 2-Amino-5-phenyl-3H-1,4-benzodiazepine 4-Oxides," J. Org. Chem, 1961, 26, pp. 4488-4497.

International Search Report issued for International Application No. PCT/IL2008/000445, dated Dec. 8, 2008.

Middleton and Alton, "Gene therapy for cystic fibrosis : which postman, which box?" Thorax 53:197-199 (1998).

* cited by examiner

□ Control group, n=6
■ Group treated with diazepam composition, n=6

* p<0.05 Nasal Brotizolam vs. Oral Brotizolam and vs. untreated control

** p<0.05 Nasal Brotizolam vs. untreated control

-■- intranasal administration of prednisolone; -▲- subcutaneous administration of prednisolone
-□- Untreated control animals -■ intranasal administration of prednisolone at 5.7mg/Kg animal;
-● intranasal administration of GA composition at a dose of 13.7mg/Kg animal;
-▲ subcutaneous administration of GA (13.7 mg/kg);
-□ Control- no treatment

- ▲ - intranasal administration of GA aqueous solution
- ☐ - no treatment

- ■ - Intranasal administration of GA; - ▲ - Subcutaneous administration of GA
control solution at a dose of 6.8 mg/kg. - ☐ - Control- no treatment -●- Intranasal administration of the compositions containing GA and CBD.
-■- Intranasal administration of GA composition.
-▲- Subcutaneous administration of GA control solution
-□- Control- no treatment

*P<0.01 Formulation A vs. Control, **P<0.05 Formulation A vs. Formulation B, ^Treatment was initiated when individual mouse developed a clinical score EAE ≥ 0.5

-□- Control- no treatment

-■- Intranasal Dexamethasone –Formulation A

-●- Intranasal Dexamethasone- Formulation B

-♦- Oral Dexamethasone- Formulation C

* P<0.001 Formulation A versus control.
A- ■ Nasally - in Nasal Delivery System- (n=3)
B- untreated group (n =3)

* P<0.001 formulation A vs. Formulation B and control
A- ■ Nasal - in our Nasal Delivery System- (n=6)
B- ■ Oral - in aqueous solution- (n=6)
C- untreated group (n =5)

\* P<0.05 Formulation A vs. formulation B and Control

-□- Control- no treatment
-■- Intranasal Glatiramer acetate- Formulation A
-▲- Intranasal Glatiramer acetate- Formulation B
-●- Subcutaneousl Glatiramer acetate- Formulation C
^ Treatment was initiated when individual mouse developed a clinical score EAE ≥ 0.5

^ ± SE (n=5). * P<0.05 Formulation A vs. Control, **P<0.05 Formulation B vs. Control -□- Control- no treatment ● Intranasal GA-CBD -Formulation A ✳ Subcutaneous GA- CBD -Formulation B ^Treatment was initiated when individual mouse developed a clinical score EAE ≥ 0.5

COMPOSITIONS FOR NASAL DELIVERY

This application is a Continuation-in-Part to International Application No. PCT/IL2006/001187, filed 15 Oct. 2006, which designated the U.S. and claims priority to U.S. Provisional Patent Application Nos. 60/907,340, filed 29 Mar. 2007, and 60/724,904, filed 11 Oct. 2005, the entire contents of each of which are hereby incorporated by reference.

Nasal drug delivery is a popular way to treat local/respiratory ailments which has traditionally been restricted to administer drugs for sinus conditions, such as congestion and allergies. Recently, however, there has been increased interest in the nose as an alternative to oral and parenteral delivery for many systemic drugs and vaccines. The vastly vascularised and immunogenic nasal mucosa present potential benefits for systemic absorption in terms of quick action, avoidance of any degradation and/or unwanted entero-hepatic metabolism of the drug (improved bio-availability) and patient compliance as well as improved immune response for vaccines. The nasal route could also provide an attractive needle-free alternative for currently injectable drugs which may improve patient compliance and allow extended use of self-medication for many chronic diseases/acute conditions or vaccinations. Some systemically-acting drugs for the treatment of osteoporosis, cardiovascular medications and painkillers are already on the market in nasal formulations.

However, although this route is beginning to be explored for systemic delivery of drugs the major limitation in nasal delivery is the insufficient permeation of drugs across the nasal mucosa. Furthermore, the anatomical and physiological features of the nose are not ideal for drug administration, since a relatively small surface area (150 cm$^2$) puts considerable constraints on formulations and drug candidates. Only very potent molecules can be used in this route. For example, for peptides there is the inverse relationship between bioavailability and molecular weight of the peptide which points toward, that those peptides with more than 30-40 amino acids require penetration enhancers for attaining a sufficient bioavailability (in the range of 10%). There are two main pathways for absorption of the molecule from the nasal cavity: paracellular (driven by passive diffusion) or transcellular (driven by carrier or receptor mediated active transport). In the absence of active transport components, most peptides cross the nasal epithelium by the paracellular route, driven by passive diffusion. Due to hydrophilicity of peptides the transcellular route is mainly relevant for transport processes or for transcytosis. Both transcellular routes are energy dependent and are therefore designated as active transport processes.

The issue of improving nasal absorption is important. Several strategies have been investigated in the past decade such as chelators of calcium (EDTA), inhibition of nasal enzymes (boro-leucin, aprotinin), inhibition of muco-ciliar clearance (preservatives), solubilisation of nasal membrane (cyclodextrin, fatty acids, surfactants) and formation of micelles (surfactants). Many surfactants such as bile acids, Laureth 9 and taurodehydrofusidate (STDHF) turned out to be quite effective in enhancing nasal absorption, but caused local cytotoxic effects on ciliated cells. Therefore, enhancers with an acceptable safety profile under chronic treatment are still to be discovered. A greater permeability of drug through nasal mucosa has the potential to overcome the limitations of oral route and to approach the benefits of intravenous infusion. Safe and efficacious enhancers will be necessary for commercially successful products.

The delivery of biologically active materials to the skin and cell membranes by means of an aqueous vehicle that comprises the combination of lipid vesicles and water miscible organic solvents has been described in the art.

For example, an aqueous carrier system containing phospholipids and ethanol was described in EP 158441, with the weight ratio between the aforementioned components being from 40:1 to 1:20.

U.S. Pat. No. 5,711,965 describes a solution comprising phospholipids, ethanol and water in a weight ratio of 10:16:74, respectively.

U.S. Pat. Nos. 5,540,934 and 5,716,638 and WO 03/000174 describe an aqueous composition containing vesicles (ethosomes) in the presence of ethanol.

U.S. Pat. No. 6,627,211 describes a carrier suitable for the administration of an anti-convulsive agent to the nasal mucous membranes. It appears that the content of organic solvents in this carrier is relatively high (30% to 60% ethanol and 30 to 60% propylene glycol).

SUMMARY OF THE INVENTION

By one aspect the present invention is based on the finding that an aqueous composition which contains phospholipids in a concentration of 0.2 to 10% by weight, in combination with one or more short chain alcohols, wherein the weight concentration of water is not less than 30% by weight and the weight concentration of the alcohol(s) is in the range between 12 to 30% by weight, may be adapted for use as an intranasal drug delivery vehicle.

Accordingly, in a first aspect, the present invention provides the use of phospholipid, one or more C2-C4 alcohols and water in the preparation of a vesicular composition adapted for intranasal administration of an active agent, wherein the concentrations of the phospholipid and the one or more alcohols in the composition are in the ranges of 0.2 to 10% and 12 to 30% by weight, respectively, and the water content of the composition is not less than 30% by weight.

Preferably, the water content in the composition is not less than 35%, and more preferably not less than 45%. The weight ratio between the alcohol(s) and the phospholipids is not less than 2:1, and more preferably not less than 5:1.

Phospholipids suitable for use in the preparation of the composition according to the present invention include phosphatidylcholine (PC), hydrogenated phosphatidylcholine, phosphatidic acid (PA), phosphatidylserine (PS), phosphatidylethanolamine (PE), phosphatidylglycerol (PPG) and phosphatidylinositol (PL). The chemical structure of phospholipids that may be used according to the present invention is described in U.S. Pat. No. 4,614,730, which is incorporated herein by reference. Preferably, the phospholipids are present in the composition of the invention at a concentration of 0.5 to 5% by weight.

The term C2-C4 alcohols, as used herein, refers to alkanols containing two, three or four carbon atoms. The alcohols to be used according to the present invention specifically include ethanol, 1-propanol, isopropyl alcohol and tert-butyl alcohol, with the former being especially preferred. The concentration of ethanol in the composition contemplated by the present invention for use as an intranasal drug delivery vehicle is preferably in the range of 15 to 27% by weight.

According to a particularly preferred embodiment of the invention, the composition further comprises one or more water miscible polyols, and especially glycols (1,2-diols, such as ethylene glycol and propylene glycol, with the latter being especially preferred), at a concentration of 1 to 30% by weight, and preferably 5 to 20 by weight.

The compositions of the present invention may be prepared by mixing together the various components, namely, water, phospholipids, one or more C2-C4 alcohols (and possibly also one or more polyols) and the active ingredient under conditions that allow the formation of vesicles. More specifically, the compositions of the present invention may be conveniently prepared by dissolving the phospholipids in the alcohol (or in the alcohol/glycol mixture), followed by the addition of the active ingredient, either in the form of an aqueous solution thereof or in a solid form, with a subsequent addition of water. The preparation of the composition is preferably carried out under stirring, typically at room temperature or at an elevated temperature, which is preferably not higher than 50° C.

Alternatively, a dispersion of the phospholipids and the active ingredient in water is prepared, into which the alcohol, optionally together with polyol (e.g., a mixture of ethanol and propylene glycol) are added with stirring, possibly under heating.

It is also possible to first prepare freeze-dried lipid vesicles having the active ingredient encapsulated therein, and subsequently dispersing the same in a mixture of water, the C2-C4 alcohol and optionally polyol.

As mentioned above, the combination of phospholipids, water, and the water-miscible organic solvents (namely, the alcohol and the polyol) according to the concentrations and weight ratios specified above allows the formation of a non-irritant, vesicular composition, with the vesicles present therein, whose size ranging between 50 nm to few microns, and more specifically, up to 5 µm, exhibiting good properties for enhanced nasal absorption. FIG. 1 is TE (transmission electron) micrograph of a specific composition according to the present invention (containing insulin as the active agent; the exact composition is given in the Examples below—entry F in table 1A). It may be seen that in this specific system, the vesicular structures are multilamellar. The vesicles were visualized by transmission electron microscopy (TEM) and scanning electron microscopy. TEM analysis was carried out using a Philips TEM CM 12 electron microscope (TEM, Eindhoven, The Netherlands) with an accelerating voltage of 100 kV.

Thus, the present invention concerns methods for intranasal administration, and compositions for intranasal administration comprising vesicular systems formed from at least one active molecule, phospholipid, alcohol (C2-C4) and water. Optionally, the composition further comprises a polyol (such as a glycol, for example propylene glycol, transcutol, tetraglycol, etc).

It has now been have found that pharmaceutical formulations including the above ingredients could deliver therapeutic amounts of agents to the systemic circulation or the brain of mammals and have efficient therapeutic or prophylaxis effect. The invention can be used for pharmaceutical, cosmetic, medical, veterinary, diagnostic and research applications. The present invention includes nasally administering to the mammal a therapeutically effective amount of active ingredient by means of compositions described above. The nasal delivery may be either for local purposes (to the mucosa of the nose), for systemic administration through the circulation or for CNS administration for curing brain disease.

It should be noted that the composition according to the present invention may include additional excipients that are well known in the art, such as surfactants, preservatives, thickening agents, co-solvents, adhesives, antioxidants, buffers, viscosity and absorption enhancing agents and agents capable of adjusting the pH and osmolarity of the formulation.

Suitable surfactants that can be used in accordance with the present invention include ionic, nonionic or amphoteric surface active agents. More specifically, hydrophilic surfactants (e.g. Tweens, Tween 80, Myrj, Brjs, Labrasol etc.) or lipophilic surfactants (eg. Span 20, Span 60, Myrj, Arlacel 83 and such) may be suitably used, preferably at a concentration in the range of 0-25% by weight.

Suitable preservatives that can be used with the present formulations include, for example, benzyl alcohol, parabens, chlorobutanol, benzalkonium salts and combinations thereof. Some examples of antioxidants include tocopherols, butyl hydroxytoluene, sodium metabisulfite, potassium metabisulfite, ascorbyl palmitate and the like. These preservatives and antioxidants may be present in the formulations in a concentration of from about 0.001% up to about 5% w/w.

Regarding buffers, the nasal delivery system may include a buffer for maintaining the formulation at a pH of about 7.0. The particular buffer, of course, can vary depending upon the particular nasal delivery system used, as well as the specific active molecule selected. Buffers that are suitable for use in the present invention include, for example, acetate, citrate, prolamine, carbonate and phosphate buffers and combinations thereof. The pharmaceutical formulations of the present invention may include a pH adjusting agent.

Regarding thickening agents, the viscosity of the formulations of the present invention can be maintained at a desired level using a pharmaceutically acceptable thickening agent. Thickening agents that can be added to the compositions of the present invention include for example, methyl cellulose, xanthan gum, tragacanth, adhesives, guar gum, carboxymethyl cellulose, hydroxypropyl cellulose, carbomer, polyvinyl alcohol, alginates, acacia, chitosans, mucoadhesive polymer-systems like poly(acrylates), cellulose derivatives, hyaluronic acid, hyaluronic acid derivatives, chitin, collagen, pectin, starch, poly(ethylene glycol), sulfated polysaccharides, carrageenan, Na-alginate, gelatin, pectin and combinations thereof. The desired concentration of the thickening agent will depend upon the agent selected and the viscosity desired.

The compositions may also comprise gel forming or bioadhesive compounds such as carbopols, alginates, scleroglucan, cellulose derivatives, starch, albumin, pluronic gels, diethyl aminoethyl (DEAE)-sephadex, polycarbophil, hyaluronic acid, hyaluronates, starch, gelatin, cholagen and others. Compositions can also be incorporated in the w/o cream, o/w cream, hydrophilic ointment or lipophilic ointment, gels, other semi-solid bases. The compositions could be delivered to the nasal cavity as drops, mists, aerosols, instillations, by use of pipetor, special devices, evaporators, vaporizators and such.

The formulations of the present invention may also include agents such as tolerance enhancers to reduce or prevent drying of the mucus membrane and to prevent irritation thereof.

The compositions according to the present invention may be applied to the nasal cavity as liquids, sprays, aerosols, nebulizers or semi-solid preparations. Semisolid preparations may be on the base of gels, w/o or o/w creams or hydrophilic/lipophilic ointments. The compositions may contain molecularly dispersed (soluble, solubilized, etc.) active agent or the fine particles/crystals of the active agent. The compositions could be administered from nasal sprays, metered-dose sprays, squeeze bottles, liquid droppers, disposable one-dose droppers, nebulizers, cartridge systems with unit-dose ampoules, single-dose pumps, bi-dose pumps, multiple-dose pumps or any other device. For example, the compositions of the invention may be stored in/delivered from a spray or aerosol device/container as described in details in Remington's Pharmaceutical Sciences (16th edition, Chapters 83 and 92).

Regarding spray devices, it should be noted that both single (unit) dose or multiple dose systems may be used. Typically, a spray device comprises a bottle and a pump; such devices are commercially available from various sources. Typically, the volume of liquid that is dispensed in a single spray actuation is in the range of from 5 to 250 microliters/each nostril/ single administration and the concentration of the active ingredient in the formulation may be readily adjusted such that one or more spray into the nostrils will comply with the dosage regimen. The present invention also provides a spray device or a dose cartridge for use in a nasal delivery device loaded with a composition as described above.

In another aspect, the invention provides a method of administering an active pharmaceutical ingredient to a patient in need thereof, which method comprises the intranasal administration of a vesicular composition comprising a therapeutically effective amount of the ingredient, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 20%, and preferably not less than 30% by weight.

Mammals include humans, pet animals, laboratory animals, farm animals and wild animals.

The intranasal drug delivery vehicle according to the present invention may be adapted for the administration of active agents that can be used for medical, pharmaceutical, veterinary, research or diagnostic purposes. However, especially preferred active agents to be used according to the present invention include an anti-diabetic agent (e.g., insulin or derivative thereof), an anti-malaria agent (which is most preferably dihydroartemisinin, DHA); an anti-anxiety agent and an anticonvulsant (which is most preferably diazepam) and anti-emetic agent (which is most preferably granisetron hydrochloride); an anti-anxiety/anti-depressant (which is most preferably buspirone hydrochloride); an anti-multiple sclerosis agent (which is most preferably glatiramer acetate, or cannabidiol {CBD}); an anti-depressant/an anti-hot flushes agent (which is most preferably paroxetine or a pharmaceutically acid addition salt thereof); an anti-dementia/ Alzheimer's agent (which is most preferably rivastigmine); and an anti-obesity agent (which is most preferably sibutramine); a hypnotic agent (which is most preferably brotizolam, or diphenhydramine hydrochloride); corticosteroids (which is most preferably prednisolone or dexamethasone), an anti-pain agent (preferably tramadol), an anti Parkinson agent (preferably apomorphine). In general, the concentration of the active pharmaceutical ingredient(s) in the composition of the present invention is preferably between 0.01 to 50%, and preferably between 0.05 to 20%. The concentration is adjusted according to the active ingredient and the dosage regime applicable therefore.

According to another aspect of the invention, especially preferred active agents to be used according to the present invention include combinations of active agents, including a combination of diazepam and diflofenac, a combination of fentanyl and diflofenac and a combination of GA and CBD.

More specifically, it has now been found that the intranasal drug delivery vehicle according to the present invention may be used for the intranasal administration of insulin. The term insulin or derivative thereof, as used herein, encompasses rapid acting (e.g. insulin aspart, insulin glulisine, insulin lispro), short-acting (regular), intermediate-acting (NPH), intermediate and short acting mixtures and long-acting insulin (e.g. insulin glargine, insuline detemir) (according to FDA classification as appears in www.fda.gov/fdac/features/2002/ chrt_insulin.html). Insulin is typically administered at daily dose of 1.5 to 150 IU.

Accordingly, in another aspect, the present invention provides a pharmaceutical composition for intranasal administration, which comprises a therapeutically effective amount of insulin or a derivative thereof together with water, phospholipids and one or more C2-C4 alcohols, wherein the concentrations of the phospholipids and the one or more alcohols are in the ranges of 0.2 to 10% and 12 to 30% by weight, respectively, with the water content of the composition being not less than 30% by weight. Preferably, the composition further comprises a polyol, and more specifically, propylene glycol, at a concentration in the range of 1 to 30% by weight.

In another aspect, the present invention provides a method for treating diabetes in a mammal, which method comprises the intranasal administration of a composition comprising a therapeutically effective amount of an anti-diabetic agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, these phospholipids forming vesicles in the composition, wherein preferably the anti-diabetic agent is insulin or derivative thereof.

It has now been also found that the intranasal drug delivery vehicle according to the present invention may be used for the intranasal administration of diazepam. Diazepam is 7-chloro-1,3-dihydro-1-methyl-5-phenyl-2H-1,4-benzo-diazepin-2-one. A method for the synthesis of diazepam has been described, for example by Sternbach L H, Reeder E, Keller O, & Metlesics W. [Quinazolines and 1,4-benzodiazepines III substituted 2-amino-5-phenyl-3H-1,4-benzodiazepine 4-oxides. J Org Chem, 26: 4488-4497, 1961]. Diazepam is typically administered at a daily dose of 0.2 to 100 mg.

Accordingly, in another aspect, the present invention provides a pharmaceutical composition, which comprises a therapeutically effective amount of diazepam together with water, phospholipids and one or more C2-C4 alcohols, wherein the concentrations of the phospholipids and the one or more alcohols are in the ranges of 0.2 to 10% and 12 to 30% by weight, respectively, with the water content of the composition being not less than 30% by weight. Preferably, the composition further comprises a polyol, and more specifically, propylene glycol, at a concentration in the range of 1 to 30% by weight.

In another aspect, the present invention provides a method for treating epileptic seizures in a mammal, which method comprises the intranasal administration of a composition comprising a therapeutically effective amount of an anti-epileptic agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition, wherein preferably the anti-epileptic agent is diazepam.

It has now been also found that it is possible to prepare a pharmaceutical composition of Granisetron [an anti-emetic agent, which is chemically named: endo-1-methyl-N-(9-methyl-9-azabicycle[3.3.1]non-3-yl)-1H-indazole-3-carboxamide] that is suitable for the intranasal administration of the drug. Granisetron is described in European Patent No. 200, 444; methods for preparing granisetron are also described in WO 03/080606. Granisetron is typically administered at a daily dose of 0.1 to 10 mg.

Accordingly, in another aspect, the present invention provides a pharmaceutical composition, which comprises a therapeutically effective amount of granisetron or a pharmaceutically acceptable salt thereof together with water, phospholipids and one or more C2-C4 alcohols, wherein the concentrations of the phospholipids and the one or more alcohols are in the ranges of 0.2 to 10% and 12 to 30% by weight, respectively, with the water content of the composition being not less than 30% by weight. Preferably, the composition further comprises a polyol, and more specifically, propylene glycol, at a concentration in the range of 1 to 30% by weight.

In another aspect, the present invention provides a method for preventing and/or treating emesis in a mammal, which method comprises the intranasal administration of a composition comprising a therapeutically effective amount of an anti-emetic agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition, wherein preferably this anti-emetic agent is granisetron.

Other compositions for intranasal administration contemplated by the present invention comprise:
(i) a therapeutically effective amount of an a pharmaceutically active ingredient selected from the group consisting of insulin, diazepam and granisetron, buspirone, glatiramer acetate, paroxetine, rivastigmine, sibutramine, tramadol, brotizolam, dephenhydramine hydrochloride, prednisolone, apomorphine, dexamethasone and cannabidiol and a pharmaceutically acceptable salt thereof, together with:
(ii) water;
(iii) phospholipids; and
(iv) one or more C2-C4 alcohols;
wherein the concentrations of the phospholipids and the one or more alcohols are in the ranges of 0.2 to 10% and 12 to 30% by weight, respectively, with the water content of the composition being not less than 30% by weight. Preferably, the composition further comprises a polyol, and more specifically, propylene glycol, at a concentration in the range of 1 to 30% by weight.

In another aspect, the present invention provides a method for preventing and/or treating obesity in a mammal, which method comprises the intranasal administration of a composition comprising a therapeutically effective amount of an anti-obesity agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition, wherein preferably the anti-obesity agent is sibutramine. Sibutramine is typically administered at a daily dose of 1 to 30 mg. Its preparation is described by Jeffery et al., [*Synthesis of Sibutramine, A Novel Cyclobutylalkylamine Useful in the Treatment of Obesity and its Major Human Metabolites, J. Chem. Soc. Perkin. Trans.* 1, 2583-2589 (1996)] and also in U.S. Pat. Nos. 4,746,680, 4,929,629 and 5,436,272.

In another aspect, the present invention provides a method for preventing and/or treating dementia in a mammal, which method comprises the intranasal administration of a composition comprising a therapeutically effective amount of an anti-dementia agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition. Preferably, the dementia is Alzheimer disease, and further preferably, this anti-dementia agent is rivastigmine.

Rivastigmine may be administered as its hydrogen tartrate salt at a daily dose of 1 to 20 mg. Its preparation is described by Rivastigmine is (S)—N-Ethyl-N-methyl-3-[1-(dimethylamino)ethyl]-phenyl carbamate hydrogen-(2R,3R)-tartrate. A method for synthesis of rivastigmine has been described for example by Bolognesi M L, Bartolini M, Cavalli A, Andrisano V, Rosini M, Minarini A, Melchiorre C. [Design, synthesis, and biological evaluation of conformationally restricted rivastigmine analogues. J Med Chem. 2004 Nov. 18; 47(24):5945-52.]. More specifically, Rivastigmine is typically administered at a daily dose of 3 to 12 mg.

In another aspect, the present invention provides a method for treating multiple sclerosis in a mammal, which method comprises the intranasal administration of a composition comprising a therapeutically effective amount of an anti-multiple sclerosis agent, phospholipids, one or more C2-C4 alcohols and water, wherein the concentrations of said phospholipids and said one or more alcohols in said composition are in the ranges of 0.2 to 10% and 12 to 30% by weight, respectively, with the water content of said composition being not less than 30% by weight, said phospholipids forming vesicles in said composition, wherein preferably the anti-multiple sclerosis agent is glatiramer acetate (GA).

Glatiramer is typically administered at a daily dose of 1 to 60 mg. Glatiramer acetate is a mixture of polypeptides composed of alanine, glutamic acid, lysine, and tyrosine in a molar ratio of approximately 4.6:1.5:3.6:1.0, respectively, which is synthesized by chemically polymerizing the four amino acids, forming products with average molecular weights ranging from about 4000 to about 13,000 daltons. The corresponding molar fractions are approximately 0.427 for alanine, 0.141 for glutamic acid, 0.337 for lysine and 0.093 for tyrosine, and may vary by about +/−10%. A method for synthesis of Glatiramer acetate has been described for example in U.S. Pat. No. 7,049,399. Glatiramer acetate is typically administered at a daily dose of 20 mg injected subcutaneously (SC).

Cannabidiol is 2-[3-Methyl-6-(1-methylethenyl)-2-cyclohexen-1-yl]-5-pentyl-1,3-benzenediol. Cannabidiol is typically administered at a daily dose of 10 to 400 mg. A method for the synthesis of cannabidiol of (−)-form has been described, for example by T. Petrzilka et al., *Helv. Chim. Acta* 52, 1102 (1969); H. J. Kurth et. al., *Z. Naturforsch.* 36B, 275 (1981); Synthesis of cannabidiol of (±)-form has been described, for example by R. Mechoulam, Y. Gaoni, *J. Am. Chem. Soc.* 87, 3273 (1965).

In another aspect, the present invention provides an inflammatory associated disease or disorder in a mammal, which method comprises the intranasal administration of a composition comprising a therapeutically effective amount of a corticosteroid agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition, wherein preferably the inflammatory associated disease or disorder is an autoimmune disease. Further preferably, the autoimmune disease is multiple sclerosis. Preferably, the corticosteroid agent is selected from dexamethasone and any pharmaceutically acceptable derivatives or salts thereof or from prednisolone and any pharmaceutically acceptable derivatives or salts thereof.

Prednisolone is 11,17-dihydroxy-17-(2-hydroxyacetyl)-10,13-dimethyl-6,7,8,9,10,11,12,13,14,15,16,17-dodecahydrocyclopenta[a]phenanthren-3-one. A method for synthesis of Prednisolone has been described for example by Kurosawa T, Ikegawa S, Chiba H, Ito Y, Nakagawa S, Kobayashi K, Tohma M. [Convenient synthesis of 18-hydroxylated cortisol and prednisolone. Steroids. 1992 September; 57(9):426-9.] Prednisolone is typically administrated at a daily dose of 5-60 mg.

Dexamethasone is 9-fluoro-11β,17,21-trihydroxy-16α-methylpregna-1,4-diene-3,20-dione. It is typically administered at a daily dose of 0.5 to 30 mg. Its preparation is described, for example, in Arth et al. J. Am. Chem. Soc. 80, 3161, (1958). Dexamethasone 21-phosphate disodium salt is Dexamethasone 21-(dihydrogen phosphate) disodium salt. A method for the synthesis of Dexamethasone 21-phosphate disodium has been described, for example by Cemerda et al. U.S. Pat. No. 2,939,873 (1960 to Merck & Co).

In another aspect, the present invention provides a method for treating depression and/or hot flushes in a mammal, which method comprises the intranasal administration of a composition comprising a therapeutically effective amount of an anti-depression agent/anti-hot flushes agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition, wherein preferably the anti-depression/anti-hot flushes agent is paroxetine or a pharmaceutically acid addition salt thereof. Paroxetine is typically administered at a daily dose of 5 to 100 mg. Its preparation is described, for example, in U.S. Pat. Nos. 6,956,121 and 6,686,473.

In another aspect the present invention provides a method for treating depression and/or anxiety in a mammal, which method comprises the intranasal administration of a composition comprising a therapeutically effective amount of an anti-depressant agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition, wherein preferably the anti-depressant agent is selected from group consisting of diazepam and buspirone hydrochloride.

Buspirone hydrochloride is N-[4-[4-(2-Pyrimidinyl)-1-piperazinyl]butyl]-8-azaspiro[4.5]decane-7,9-dione hydrochloride. Buspirone is typically administered at a daily dose of 15 to 30 mg. Patients should not take a total dose of more than 60 mg daily. Methods of synthesis of buspirone or its derivatives are disclosed in, or can be easily adapted by one of ordinary skill in organic synthesis, from procedures disclosed in Wu, et al, Ger. Patent No. 2,057,845, and U.S. Pat. No. 3,717,634. See also J. Clin. Psychiat. 43, 1-116 (1982).

In another aspect the present invention provides a method for preventing and/or treating pain in a mammal, which method comprises the intranasal administration of a composition comprising a therapeutically effective amount of an analgesic agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition, wherein preferably the analgesic agent is tramadol or a pharmaceutically acceptable salt thereof.

Tramadol hydrochloride is (±)cis-2-[(dimethylamino)methyl]-1-(3-methoxyphenyl)cyclohexanol hydrochloride. Tramadol is typically administrated at a daily dose of from 50 mg daily dose but not exceeding 400 mg per day. Its preparation is described, for example, in J. Mex. Chem. Soc. 2005, 49(4), 324-327, or by K. Flick et al Arzneim.-Forsch./Drug Res., 1978, 28, 107-113, or by Pat. Brit. 997399, 1965; U.S. Pat. No. 3,652,589.

In another aspect the present invention provides a method for inducing sleep and/or preventing insomnia in a mammal, which method comprises the intranasal administration of a composition comprising a therapeutically effective amount of a hypnotic agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition, wherein preferably the hypnotic agent is brotizolam and any pharmaceutically acceptable salt thereof, or diphenhydramine hydrochloride and any pharmaceutically acceptable salt thereof.

Brotizolam is 8-bromo-6-(o-chlorophenyl)-1-methyl-4H-s-triazolo[3,4c]thieno[2,3e]1,4-diazepine. A method for its synthesis has been described, for example in Japanese Patent Unexamined Publication No. 80899/1976(S51) (U.S. Pat. No. 4,094,984). Brotizolam is typically administered at a daily dose of 0.01 to 1 mg.

In another aspect, the present invention provides a method for treating parkinson in a mammal, which method comprises the intranasal administration of a composition comprising a therapeutically effective amount of an anti-parkinson agent, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition, wherein preferably the anti-parkinson agent is apomorphine.

Apomorphine is (6aR)-5,6,6a,7-Tetrahydro-6-methyl-4H-dibenzo[de,g]quinoline-10,11-diol; A method for the total synthesis of Apomorphine of (±)-form has been described, for example by J. L. Neumeyer et. al., J Pharm. Sci. 59, 1850 (1970); of (+)-form and (−)-form: V. J. Ram, J. L. Neumeyer; J. Org. Chem. 46, 2830 (1981). Apomorphine is typically administrated at a daily dose of 0.5 to 100 mg.

Another aspect of the present invention is related to the treatment of malaria. In malaria prevalent regions of the world, Plasmodium infections is the reason for a very high mortality rates (hundreds of thousands of deaths), especially among children. Many patients with acute malaria are unable to tolerate oral therapy and parenteral treatment, which could only be available at hospitals, is necessary. However, these amenities are usually inaccessible.

It has now been found that anti-malaria drug administered intranasally is effective at least as or even more that intraperitoneally administration. This finding paves the way to the formulation of a pharmaceutical composition for intra-nasal administration comprising a carrier and at least one anti-malaria agent. Examples of anti-malaria drugs are artemisinin derivatives, dihydroartemisinin, artemotil, chloroquine, primaquine, doxycillin, quinine, aminoquinolines, cinchona alkaloids, antifolates, quinidine, melfoquine, halofantrine, lumefantrine, amodiaquine, pyronaridine, tafenoquine, artesunates, artemether, artemotil, biguanides, proguanil, chloroproguanil, diaminopyrimidines, pyremethamine, trimethoprim, dapsone, sulfonamides, atovaquone, sulfadoxine-pyrimethamine, N-acetyl cysteine, piperaquine, DHA-piperaquine, lumefantrine, dermaseptins, bisphosphonates, quercitin etc.

The present invention is thus also concerned with a pharmaceutical composition for intra-nasal administration comprising a carrier and at least one anti-malaria drug, wherein the carrier is most preferably a vesicular carrier (namely, a carrier that contain vesicles suspended therein), and also with the use of an anti-malaria agent in the preparation of a medicament for intra-nasally treating malaria.

The intranasal composition may comprise any carrier or combination of carriers known to be suitable for intranasal administration. Preferably, however, the composition in accordance with this aspect of the invention comprises at least one anti malaria agent in combination with the intranasal drug delivery vehicle as described above, which vehicle comprises not less than 30% by weight water, from 12 to 30% by weight C2-C4 alcohol(s), from 1 to 30% by weight water-miscible polyol(s), from 0.2 to 10% phospholipids arranged in a vesicular structure. Other preferred features of the anti-malaria composition are as described above in connection with the intranasal drug delivery vehicle.

By another aspect the present invention provides a method for treating malaria in a mammal, which method comprises the intranasal administration of a composition comprising a therapeutically effective amount of an anti-malaria drug, phospholipids, one or more C2-C4 alcohols and water, wherein the concentrations of the phospholipids and the one or more alcohols in the composition are in the ranges of 0.2 to 10% and 12 to 30% by weight, respectively, with the water content of the composition being not less than 30% by weight, the phospholipids forming vesicles in the composition. Preferably, the anti-malaria drug is an artemisinin derivative, more preferably—the anti-malaria drug is dihydroartemisinin, which is typically administered at the following dosage regimen: Adults: 40-120 mg/day in divided doses for 6-7 days; Children: 2-4 mg/kg in a divided loading dose on the first day followed by 1-2 mg/kg daily for 6 days. Dihydroartemisinin can be prepared by reduction of artemisinin with sodium borohydride; [A. Brossi et al., Arteether, a New Antimalarial Drug: Synthesis and Antimalarial Properties, J. Med. Chem. 31, 645-650 (1988)].

As used herein, nasally administering or nasal administration includes administering the compositions into nostrils of the nose to the mucous membranes of the nasal passage or nasal cavity of the mammal. Such formulations can be administered, for example, as a nasal spray, nasal inhaler, nasal drop, aerosol, propellants, pressured dispersion, aqueous aerosol, nebulizer, nasal suspension, instillation, nasal gel, nasal ointment and nasal cream by aid of any new or old type device. Administration of compositions of the present invention may also take place using a nasal tampon or nasal sponge containing the compositions.

Active ingredient can also be brought into a viscous base by adding to the above delivery systems conventionally used ingredients such as natural gums, cellulose and derivatives, acrylic polymers (eg. carbopol) and vinyl polymers (polyvinylpyrrolidone), scleroglucans, xylan, alginates, calcium alginate, hyaluronates, collagenates, starch gels, gelatin systems, kitosan carriers.

It should be understood that the intranasal drug delivery vehicle according to the present invention is not limited for the administration of the specific active ingredients mentioned above. It should be noted that the active agent can be a chemically defined synthetic molecule, a naturally derived or synthetic peptide, a protein, a polysaccharide, or a nucleic acid such as RNA or DNA. The active agent may also be referred to as active compound, drug, drug substance, medicinal substance, therapeutic agent, and the like. The active agents that could be delivered by means of the above compositions alone or in combinations are without being limited:

Antimalarial agents (e.g. artemisinin derivatives, dihydroartemisinin, artemotil, chloroquine, primaquine, doxycillin, quinine, aminoquinolines, cinchona alkaloids, antifolates, quinidine, melfoquine, halofantrine, lumefantrine, amodiaquine, pyronaridine, tafenoquine, artesunates, artemether, artemotil, biguanides, proguanil, chloproguanil, diaminopyrimidines, pyremethamine, trimethoprim, dapsone, sulfonamides, atovaquone, sulfadoxine-pyrimethamine, N-acetyl cysteine, piperaquine, DHA-piperaquine, lumefantrine, dermaseptins, bisphosphonates, quercitin etc. The drugs could be used alone or in combinations.)

OTC drugs (e.g. antipyretics, anesthetics, cough suppressants, etc.)

Antiinfective agents

Anti-malaria agents (such as dihydroartemisinin, etc.)

Antibiotics (e.g. penicillins, cephalosporins, macrolids, tetracyclines, aminoglycosides, anti-tuberculosis agents, doxycycline, ciprofloxacine, moxifloxacine, gatifloxacine, carbapenems, azithromycine, clarithromycine, erythromycine, ketolides, penems, tobramyicin, filgrastim, pentamidine, microcidin, clerocidin; amikacine, etc.)

Antifungal/Antimycotic (metronidazole, ketoconazole, itraconazole, voriconazole, clotrimazole, bifonazole, fluconazole, amphotericine B, natamycine, nystatine, ciclopiroxolamine, etc.)

Genetic molecules (e.g. Anti-sense oligonucleotides, nucleic acids, oligonucleotides, DNA, RNA, Anti-cancer agents (e.g. anti-proliferative agents, anti-vascularization agents, taxol, etopside, cisplatin, etc.)

Anti-protozoal agents

Antivirals (e.g. acyclovir, gancyclovir, ribavirin, anti-HIV agents, anti-hepatitis agents, famciclovir, valaciclovir, didanosine, saquinavir, ritonavir, lamivudine, stavudine, zidovudine, etc.)

Anti-inflammatory drugs (e.g. NSAIDs, steroidal agents, cannabinoids (in particular cannabidiol), leukotriene-antagonists, tacrolimus, sirolimus, everolimus, etc.)

Anti-allergic molecules (e.g. antihistamines, fexofenadine)

Bronchodilators

Vaccines and other immunogenic molecules (e.g. tetanus toxoid, reduced diphtheria toxoid, acellular pertussis vaccine, mums vaccine, smallpox vaccine, anti-HIV vaccines, hepatitis vaccines, pneumonia vaccines, influenza vaccines, TNF-alpha-antibodies etc.)

Anesthetics, local anesthetics.

Antipyretics (e.g. paracetamol, ibuprofen, diclofenac, aspirin, etc.)

Agents for treatment of severe events such cardiovascular attacks, seizures, hypoglycemia, etc.

Aphrodisiacs from plants or synthetics

Anti-nausea and anti-vomiting.

Immunomodulators (immunoglobulins, etc.)
Cardiovascular drugs (e.g. beta-blockers, alpha-blockers, calcium channel blockers, etc.)
Peptide and steroid hormones (eg. insulin, insulin derivatives, insulin detemir, insulin monomeric, oxytocin, LHRH, LHRH analogues, adreno-corticotropic hormone, somatropin, leuprolide, calcitonin, parathyroid hormone, estrogens, testosterone, adrenal corticosteroids, megestrol, progesterone, sex hormones, growth hormones, growth factors, etc.)
Peptide and protein related drugs (e.g. amino acids, peptides, polypeptides, proteins)
Vitamins (e.g. Vit A, Vitamins from B group, folic acid, Vit C, Vit D, Vit E, Vit K, niacin, derivatives of Vit D, etc.)
Autonomic Nervous System Drugs
Fertilizing agents
Antidepressants (e.g. buspirone, venlafaxine, benzodiazepins, selective serotonin reuptake inhibitors (SSRIs), sertraline, citalopram, tricyclic antidepressants, paroxetine, trazodone, lithium, bupropion, sertraline, fluoxetine, etc.)
Agents for smoking cessation (e.g. bupropion, nicotine, etc.)
Agents for treating alcoholism and alcohol withdrawal
Lipid-lowering agents (eg. inhibitors of 3 hydroxy-3-methylglutaryl-coenzyme A (HMG-CoA) reductase, simvastatin, atrovastatin, etc.)
Drugs for CNS or spinal cord (benzodiazepines, lorazepam, hydromorphone, midazolam, Acetaminophen, 4'-hydroxyacetanilide, barbiturates, anesthetics, etc.)
Anti-epilepsic agents (e.g. valproic acid and its derivatives, carbamazepin, etc.)
Angiotensin antagonists (e.g. valsartan, etc.)
Anti-psychotic agents and anti-schizophrenic agents (e.g. quetiapine, risperidone)
Agents for treatment of Parkinsonian syndrome (e.g. L-dopa and its derivatives, trihexyphenidyl, etc.)
Anti-Alzheimer drugs (e.g. cholinesterase inhibitors, galantamine, rivastigmine, donepezil, tacrine, memantine, N-methyl D-aspartate (NMDA) antagonists).
Agents for treatment of non-insulin dependent diabetes (e.g. metformine),
Agents against erectile dysfunction (e.g. sildenafil, tadalafil, papaverine, vardenafil, PGE1, etc.)
Prostaglandins
Agents for bladder dysfunction (e.g. oxybutynin, propantheline bromide, trospium, solifenacin succinate etc.)
Agents for treatment menopausal syndrome (e.g estrogens, non-estrogen compounds, etc.)
Agents for treatment hot flushes in postmenopausal women
Agents for treatment primary or secondary hypogonadism (e.g. testosterone, etc.)
Cytokines (e.g. TNF, interferons, IFN-alpha, IFN-beta, interleukins etc.)
CNS stimulants
Muscle relaxants
Anti paralytic gas agents
Appetite stimulators/depressors (e.g. cannabinoids, etc.)
Gastrointestinal absorption modifiers
Narcotics and Antagonists (e.g. opiates, oxycodone etc.)
Painkillers (opiates, endorphins, tramadol, codein, NSAIDs, gabapentine etc.)
Hypnotics (Zolpidem, benzodiazepins, barbiturates, ramelteon, brotizolam, diphenhydramine hydrochloride, etc.)
Histamines and Antihistamines
Antimigraine Drugs (e.g. imipramine, propranolol, sumatriptan, eg.)
Diagnostic agents (e.g. Phenolsulfonphthalein, Dye T-1824, Vital Dyes, Potassium Ferrocyanide, Secretin, Pentagastrin, Cerulein, etc.)
Topical decongestants or anti-inflammatory drugs
Anti-acne agents (e.g. retinoic acid derivatives, doxicillin, minocyclin, etc.)
ADHD related medication (e.g. methylphenidate, dexmethylphenidate, dextroamphetamine, d- and l-amphetamin racemic mixture, pemoline, etc.)
Diuretic agents
Anti-osteoporotic agents (e.g. bisphosphonates, aledronate, pamidronate, tirphostins, etc.)
Drugs for treatment of asthma
Anti-Spasmotic agents (e.g. papaverine, etc.)
Agents for treatment of multiple sclerosis and other neurodegenerative disorders (eg. mitoxantrone, glatiramer acetate, interferon beta-1a, interferon beta-1b, etc.)
Plant derived agents from leave, root, flower, seed, stem or branches extracts.

By another aspect the present invention is based on the finding that at least two active agents may exert their beneficial effect while using the formulation of the invention.

Thus the present invention concerns use of a carrier comprising not less than 30% by weight water, from 12 to 30% by weight C2-C4 alcohol(s), from 1 to 30% by weight water-miscible polyol(s), from 0.2 to 10% phospholipids arranged in a vesicular structure and therapeutically effective amount of at least one pharmaceutically active ingredient, in the preparation of a pharmaceutical composition suitable for intranasal administration.

By one embodiment the above use is of at least two pharmaceutically active ingredients, and by a preferred embodiment the use of two pharmaceutically active ingredients.

By yet another aspect the present invention is based on the finding that specific combinations of two pharmaceutically active ingredients are advantageous in treating diseases.

Thus the present invention concerns a pharmaceutical composition comprising a combination of diazepam and diclofenac and a pharmaceutically acceptable carrier.

The present invention also concerns a pharmaceutical composition for the treatment and/or prevention of pain comprising as an active ingredient a combination of diazepam and diclofenac and a pharmaceutically acceptable carrier.

Diclofenac is 2-(2-(2,6-dichlorophenylamino)phenyl)acetic acid. A method for synthesis of diclofenac has been described for example by A. Sallman, R. Pfister, U.S. Pat. No. 3,558,690, (1971). Diclofenac is typically administered at a daily dose of 25-150 mg.

Preferably the pharmaceutical composition is adapted for nasal administration.

Most preferably the present invention concerns a pharmaceutical composition adapted for intranasal administration comprising a combination of diazepam and diclofenac and a carrier comprising not less than 30% by weight water, from 12 to 30% by weight C2-C4 alcohol(s), from 0.2 to 10% phospholipids arranged in a vesicular structure and preferably further comprises from 1 to 30% by weight water-miscible polyol(s).

By another aspect the present invention concerns a pharmaceutical composition comprising a combination of diclofenac and fentanyl, and a pharmaceutically acceptable carrier.

The present invention also concerns a pharmaceutical composition for the treatment and/or prevention of pain comprising as an active ingredient a combination of diclofenac and fentanyl, and a pharmaceutically acceptable carrier. Fentanyl is N-(1-phenethyl-4-piperidyl)-N-phenyl-propanamide. Fentanyl is typically administered at a daily dose of 100 to 400 mg. Its preparation is described, for example, in Gupta, P. K et al., J. Chem. Res. 2005, 7, 452-453 and in Def. Res. Dev. Establ., Gwalior 474 002, India; Eng.) R. Staver.

Preferably the pharmaceutical composition is adapted for nasal administration.

Most preferably the present invention concerns a pharmaceutical composition adapted for intranasal administration comprising a combination of fentanyl and diclofenac and a carrier comprising not less than 30% by weight water, from 12 to 30% by weight C2-C4 alcohol(s), from 0.2 to 10% phospholipids arranged in a vesicular structure, preferably further comprises from 1 to 30% by weight water-miscible polyol(s).

The present invention provides concerns a pharmaceutical composition comprising a combination of glatiramer acetate and cannabidiol and a pharmaceutically acceptable carrier.

By another aspect the present invention concerns a method for treating multiple sclerosis in a mammal, which method comprises the intranasal administration of a composition comprising an anti multiple sclerosis agent, such as glatiramer acetate, and cannabidiol, water, phospholipids and one or more C2-C4 alcohols, wherein the concentrations of the phospholipids and the one or more alcohols are in the ranges of 0.2 to 10% and 12 to 30% by weight, respectively, with the water content of the composition being not less than 30% by weight. Preferably the composition further comprises water-miscible polyol(s) in a concentration of 1 to 30%.

The present invention also concerns a pharmaceutical composition for the treatment of multiple sclerosis comprising the combination of cannabidiol and an anti multiple sclerosis agent, such as glatiramer acetate, and a pharmaceutically acceptable carrier. The carrier is preferably adapted for nasal or parenteral administration. The carrier may thus be in a liquid form (including viscous liquids), or semi-solid (e.g., a gel, cream). A carrier which comprises water, one or more C2-C4 alcohols and phospholipids has been found to be especially suitable in this regard. The cannabidiol and the glatiramer acetate are preferably present in the composition in synergistically effective amounts. More specifically, the concentration of cannabidiol and glatiramer acetate are within the range of 0.5-40% and 0.5-30%, respectively.

Most preferably the present invention concerns a pharmaceutical composition adapted for intranasal administration comprising a combination of glatiramer acetate and cannabidiol and a carrier comprising not less than 30% by weight water, from 12 to 30% by weight C2-C4 alcohol(s), from 1 to 30% by weight water-miscible polyol(s), from 0.2 to 10% phospholipids arranged in a vesicular structure. The C2-C4 alcohol is preferably ethanol, and the composition may further comprise a polyol such as propylene glycol.

By another aspect the present invention concerns a method for regenerating neurons and/or cells in a brain in a mammal in a mammal, which method comprises the intranasal administration of a composition comprising glatiramer acetate, cannabidiol, water, phospholipids water-miscible polyol(s), and one or more C2-C4 alcohols, wherein the concentrations of the phospholipids and the one or more alcohols are in the ranges of 0.2 to 10%, 1 to 30% and 12 to 30% by weight, respectively, with the water content of the composition being not less than 30% by weight.

IN THE DRAWINGS

Figure 13:
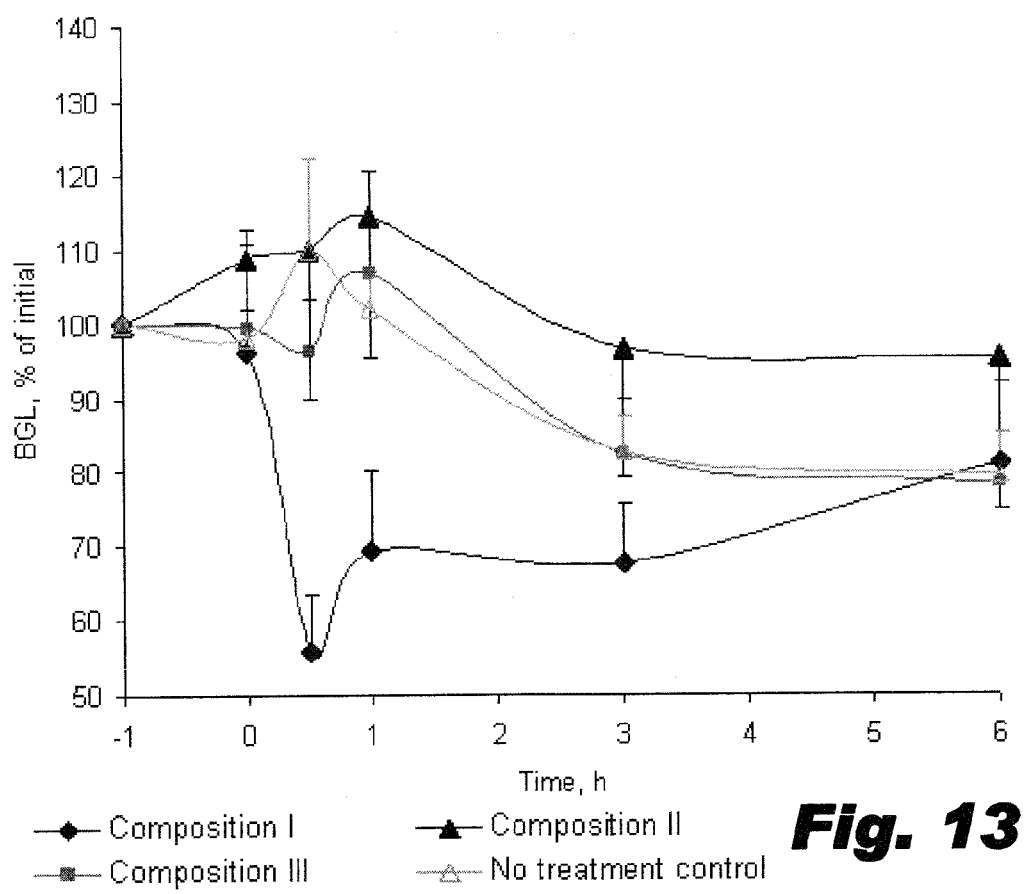
Figure 14:
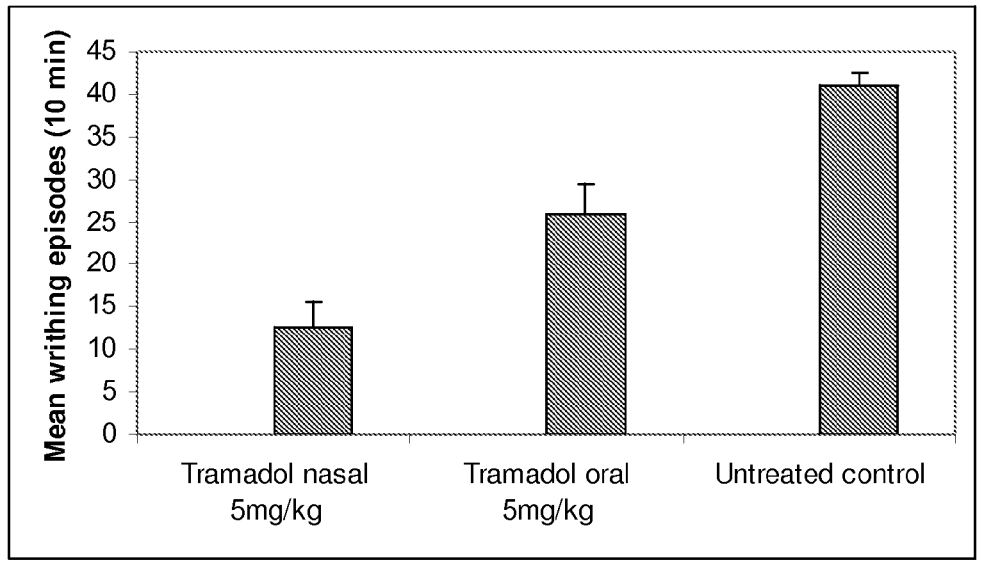
Figure 15:
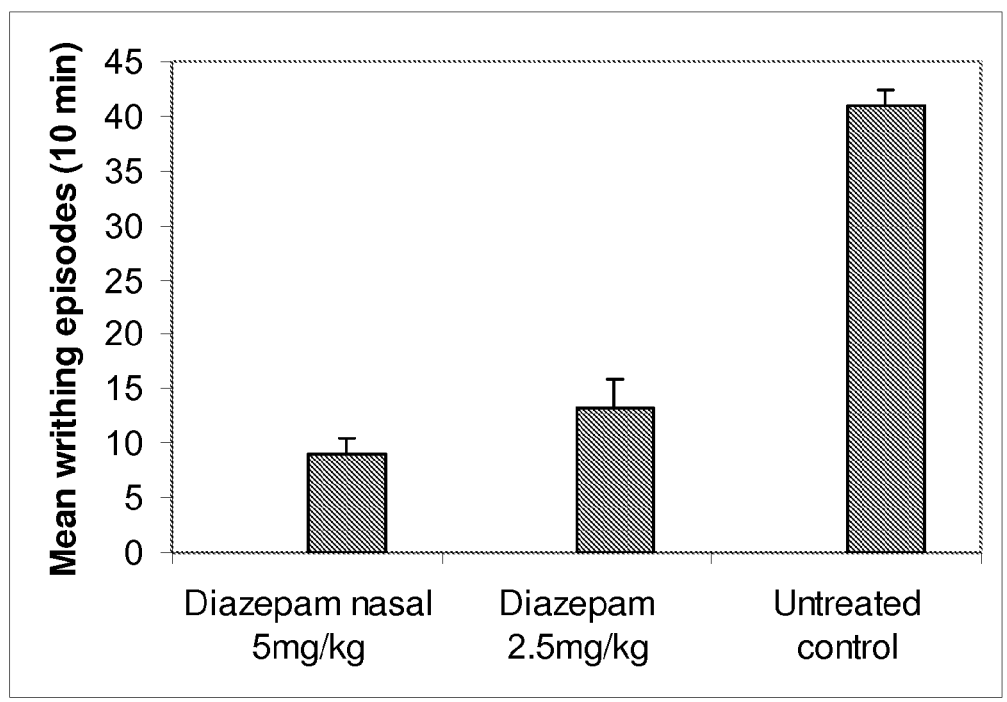
Figure 17:
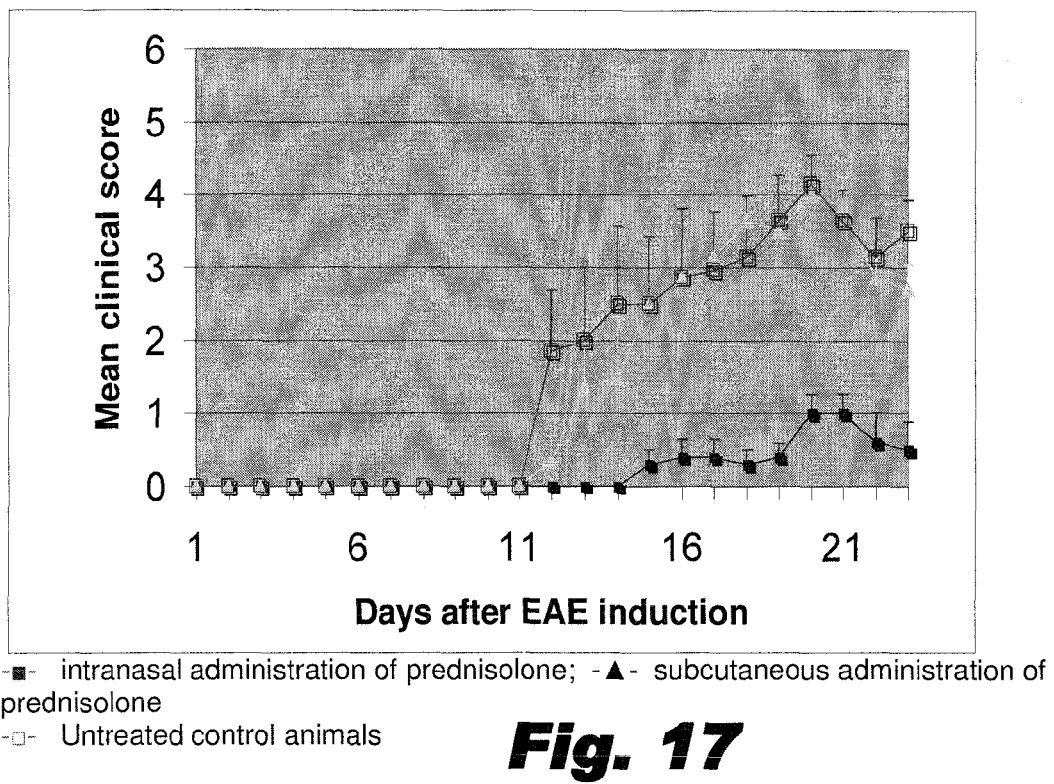
Figure 18:
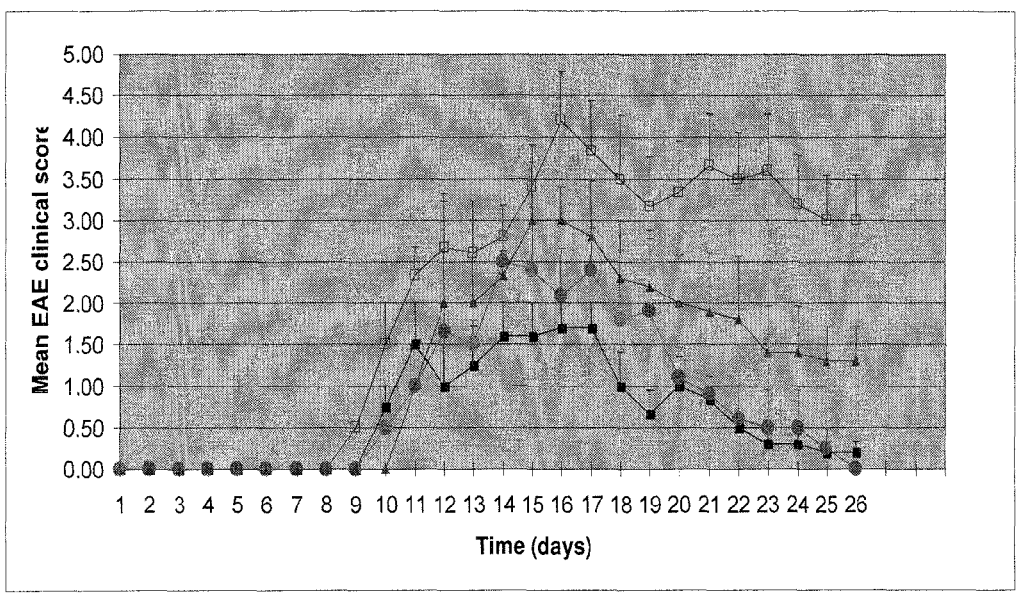
Figure 19:
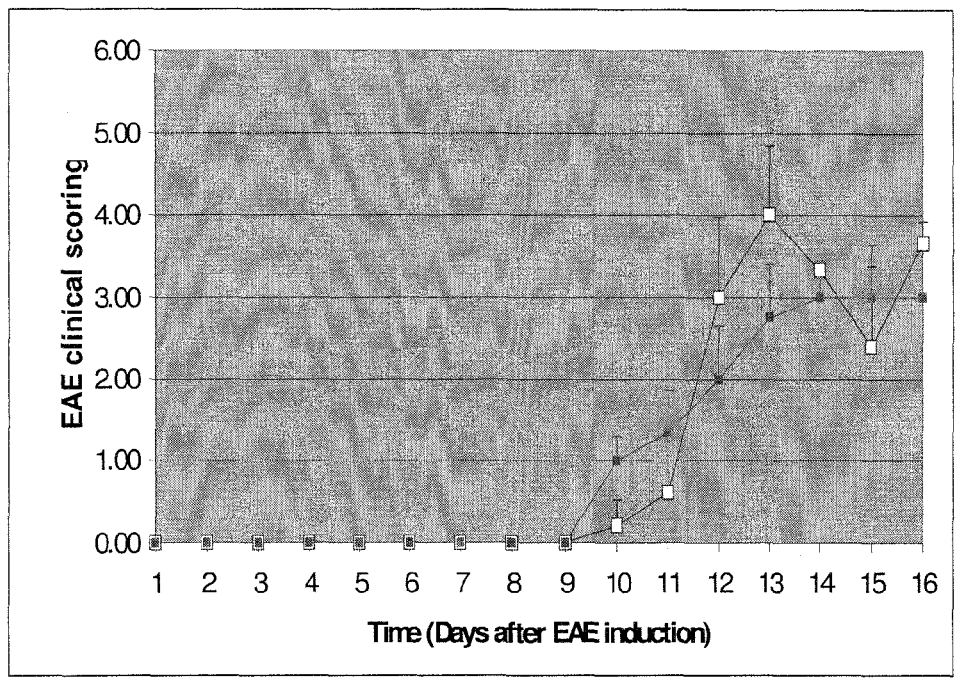
Figure 20:
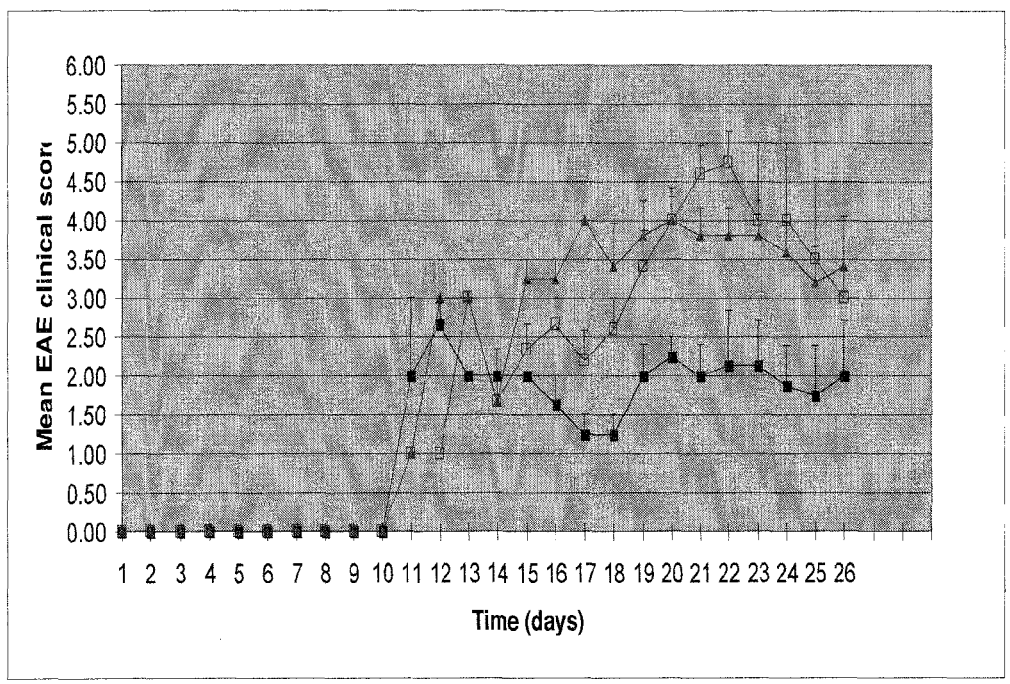
Figure 21:
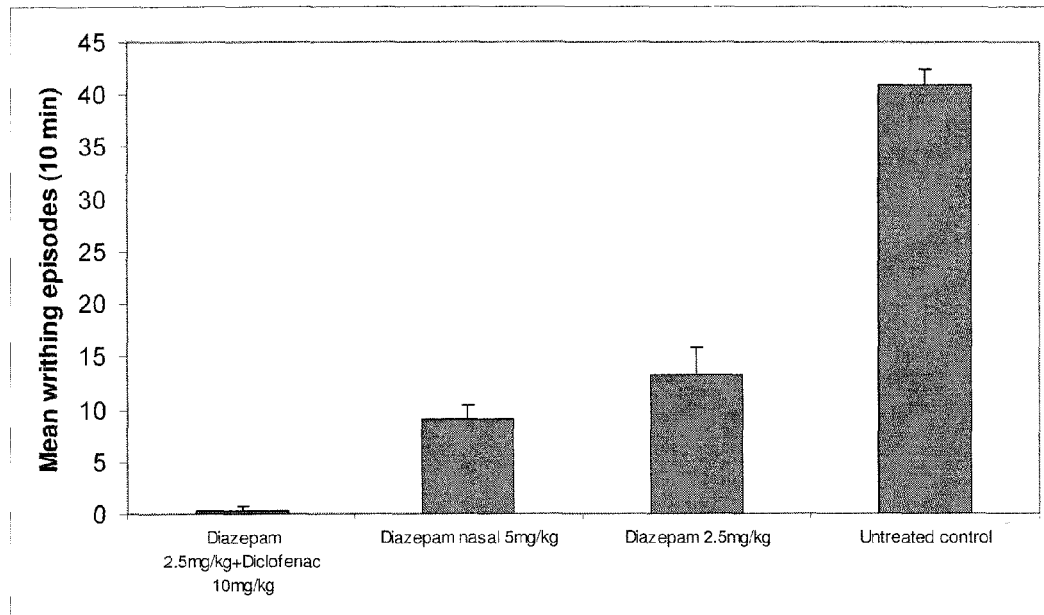
Figure 22:
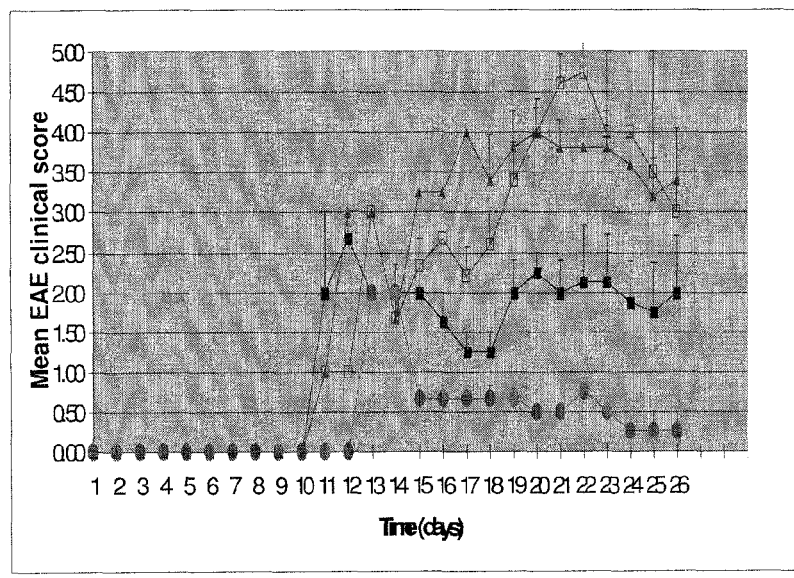
Figure 23:
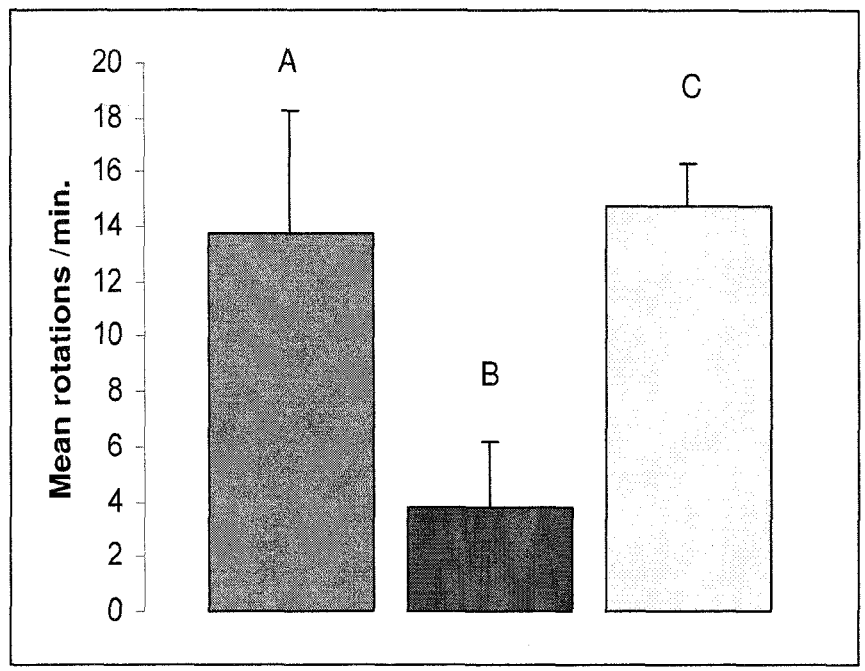
Figure 24:
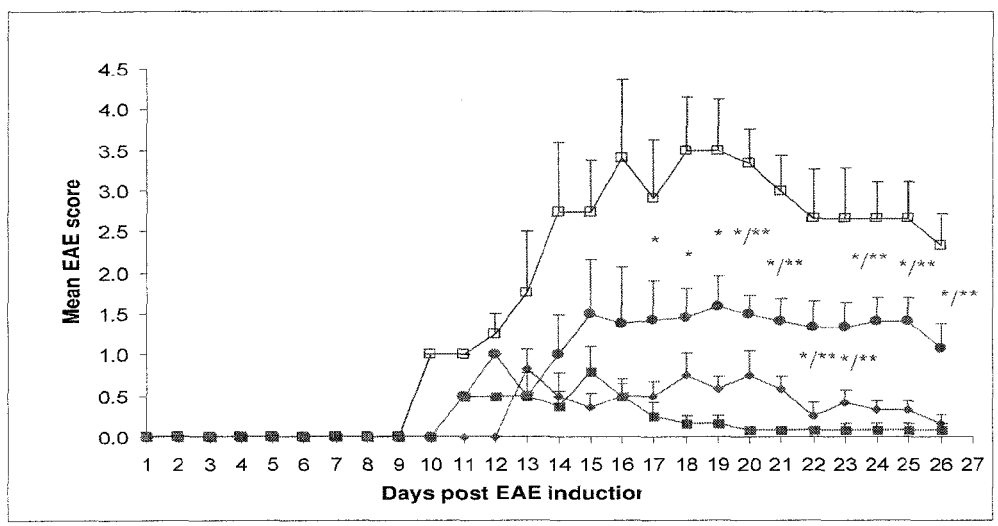
Figure 25:
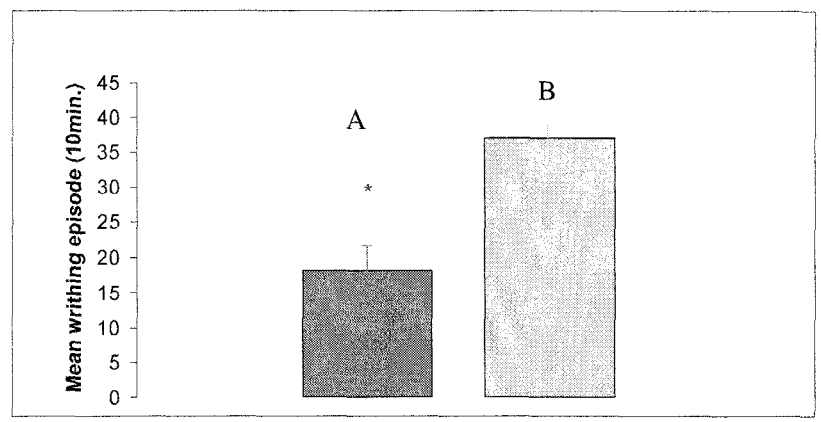
Figure 26:
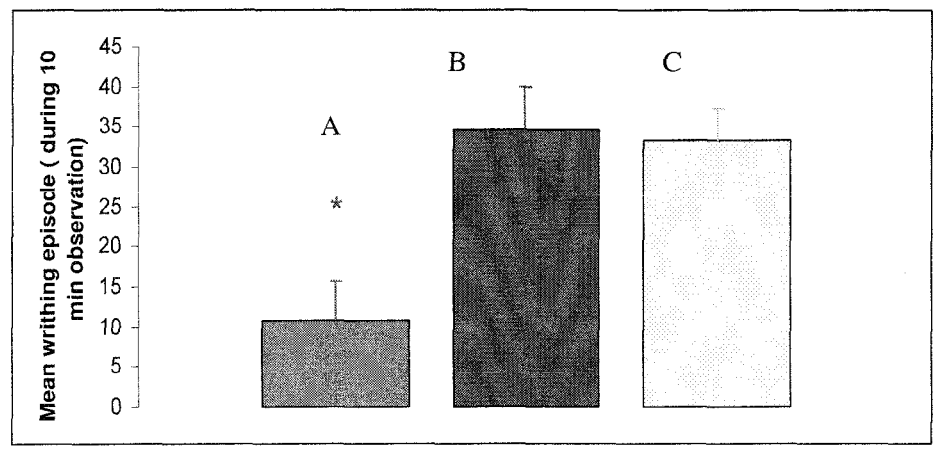
Figure 27:
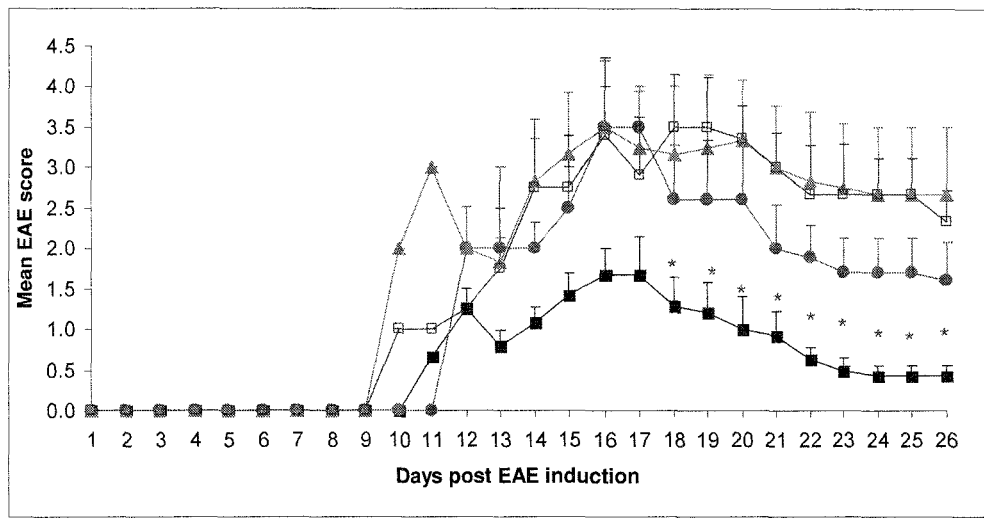
Figure 28:
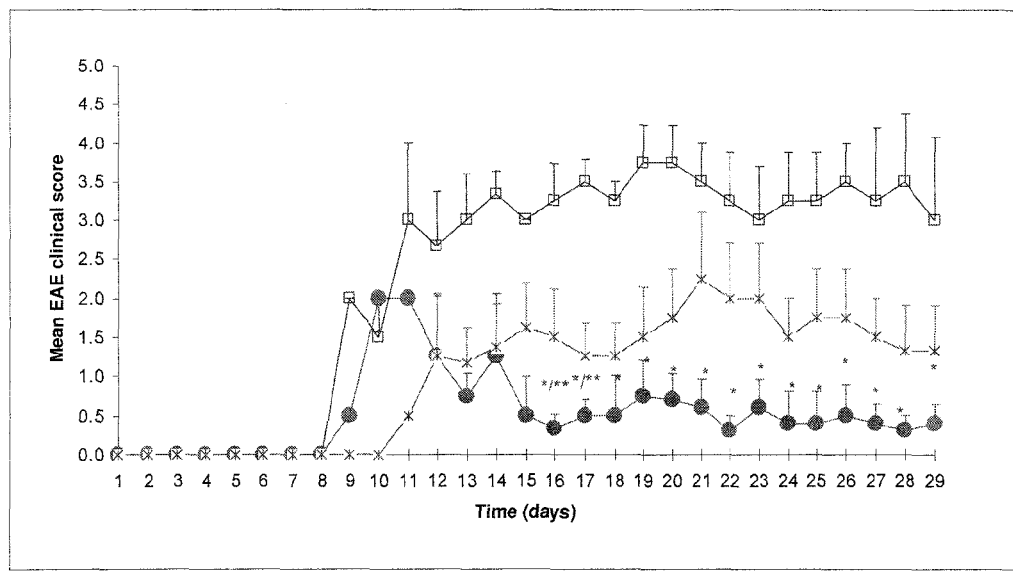

FIG. 13 is a graph showing blood glucose levels (% of initial) in mice following intranasal administration of 25 μL of insulin compositions in a comparative study, whereas the concentration of human insulin in all compositions is 63 IU/mL: composition I being a composition of the invention, composition II being a control composition having only 10% EtOH and composition III being a liposomal control composition;

FIG. 14 is a bar diagram showing the results of a writhing test in mice following nasal administration of tramadol HCl (drug dose 5 mg/kg) as compared to oral administration of an aqueous drug solution (same drug dose) and versus untreated control;

FIG. 15 is a bar diagram showing the results of a writhing test in mice following nasal administration of diazepam (drug dose 5 mg/kg or 2.5 mg/kg) as compared to untreated control;

FIGS. 16A-B are bar diagrams showing the latency (FIG. 16A) and total sleeping time (FIG. 16B) in mice following nasal administration of brotizolam (drug dose 0.25 mg/kg or 2.5 mg/kg), 5 minutes prior to sleep induction with pentobarbitone sodium (40 mg/kg), as compared to oral administration of an aqueous drug solution (at the sane dosage) and versus untreated control;

FIG. 17 is a graph showing clinical manifestations of Experimental Allergic Encephalomyelitis (EAE) induced by Myelinoligodendrocyte glycoprotein (MOG peptide) (n=6) for prophylactic intranasal administration of prednisolone composition at a dose of 3 mg/Kg animal, as compared to subcutaneous administration of aqueous drug solution (at the sane dosage) and versus untreated control;

FIG. 18 is a graph showing clinical manifestations of EAE induced by MOG peptide for intranasal administration of prednisolone composition at a dose of 5.7 mg/Kg animal and 13.7 mg/Kg animal, as compared to subcutaneous administration of an aqueous drug solution (at 13.7 mg/kg) and versus untreated control;

FIG. 19 is a graph showing clinical manifestations of EAE in mice following nasal administration of glatiramer acetate (GA, Copaxone®) at a dose of 13.7 mg/Kg animal, versus untreated control;

FIG. 20 is a graph showing clinical manifestations of EAE in mice following nasal administration of GA at a dose of 6.8 mg/Kg animal, as compared to subcutaneous administration of aqueous drug solution (at the same dose) and versus untreated control;

FIG. 21 is a bar diagram showing the results of a writhing test in mice following nasal administration of an amalgam composition of diazepam and/or diclofenac, versus untreated control;

FIG. 22 is a graph showing clinical manifestations of EAE following intranasal administration of a low dose of GA, as compared to subcutaneous injection of the same dose of GA;

FIG. 23 is a bar diagram showing rotational behavior in rats following nasal administration of apomorphine, formulation A (A), versus nasal administration of apomorphine formulation B (A) and nasal subcutaneous administration of apomorphine formulation C(C);

FIG. 24 is a graph showing clinical manifestations of EAE following intranasal administration of Dexamethasone, versus oral administration thereof and untreated control;

FIG. 25 is a bar diagram showing the results of a writhing test in mice following nasal administration of tramadol HCl (drug dose 5 mg/kg, A) versus untreated control (B);

FIG. 26 is a bar diagram showing the results of a writhing test in mice following nasal administration of tramadol HCl (drug dose 5 mg/kg, A) versus aqueous solution (B) and untreated control (C);

FIG. 27 is a graph showing clinical manifestations of EAE following intranasal administration of Glatiramer acetate, versus subcutaneous administration thereof and untreated control; and FIG. 28 is a graph showing clinical manifestations of EAE following intranasal administration of CBD and GA, versus subcutaneous administration thereof and versus untreated control.

EXAMPLES

Materials

Insulin solution used for preparation of the compositions C-V is Biosynthetic Human Insulin aqueous solution 100 IU/mL (Actrapid, Novartis).

Example 1

Insulin-Containing Composition 20 mg of phospholipids (Phospholipon 90, Natterman) were dissolved in 0.3 grams ethanol (J. T. Baker) and to this solution 0.1 grams propylene glycol was added. The obtained solution was added slowly to the 0.58 grams of the aqueous solution of human insulin (100 IU/mL) under constant stirring at room temperature. The composition was stirred for additional 5 minutes. It is also possible to introduce the aqueous human insulin solution into the phospholipid solution in ethanol and propylene glycol. The final composition contained 58 IU insulin/gram.

Example 2

Insulin-Containing Composition 15 mg of phospholipids (Phospholipon 90) were dissolved in a mixture of 225 mg ethanol and 75 mg propylene glycol. To the obtained solution, 685 mg of aqueous solution of insulin (100 IU/mL) were added slowly under constant stirring at 40° C. The composition was stirred for additional 5 minutes. The final composition contained 68.5 IU insulin/gram. This composition is also prepared at room temperature.

Example 3

Insulin-Containing Composition

To freeze-dried liposomes containing 40 mg phospholipid and 116 IU human insulin a mixture of 0.6 grams EtOH, 0.2 grams propylene glycol (PG) and 1.16 grams DDW was added in aliquots under constant stirring at room temperature. The composition was stirred for additional 5 minutes. The final composition contained 58 IU insulin/gram (1.45 IU insulin/25 microliter).

Example 4

Insulin-Containing Composition

To a liposomal dispersion containing 30 mg phospholipid, 137 IU insulin and 685 mg DDW, 225 mg EtOH and 75 mg propylene glycol were added under constant stirring at room temperature. The composition was stirred for additional 5 minutes. The final composition contained 68.5 IU insulin/gram.

Example 5

Insulin-Containing Composition 0.05 grams Carbopol 974P was dispersed in 1 mL of insulin aqueous solution (100 IU/mL). In a separate container 0.5 grams of Phospholipon 90 and 0.15 grams of cholesterol were dissolved in 1.85 grams ethanol and to this solution 0.95 grams propylene glycol were added. To this mixture 0.65 grams Tween 20 were added. To the obtained system 4.8 mL of insulin aqueous solution (100 IU/mL) were added slowly under constant stirring at room temperature in a Heidolph mixer (at 650 rpm). The composition was stirred for additional 5 minutes. This phase was slowly added to Carbopol dispersion in insulin aqueous solution under constant mixing at 400 rpm. To the obtained system 0.05 grams triethanolamine (TEA) were added slowly under constant mixing at 400 rpm.

Example 6

Insulin-Containing Composition 0.01 grams Carbopol 974P were dispersed in 1.18 mL of DDW. In a separate container 0.5 grams of phospholipids (Phospholipon 90) and 0.02 grams ceramide were dissolved in 1.48 grams ethanol and to this solution 1 gram propylene glycol was added. To the obtained system 5.8 mL of insulin aqueous solution (100 IU/mL) were added slowly under constant stirring at room temperature in Heidolph mixer (650 rpm). The composition was stirred for additional 5 minutes. This phase was slowly added to Carbopol dispersion in DDW under constant mixing at 400 rpm. To the obtained system 0.01 grams triethanolamine (TEA) were added slowly under constant mixing at 400 rpm.

Example 7

Dihydroartemisinin-Containing Compositions

Dihydroartemisinin (DHA) compositions, described below, were prepared by dissolving phospholipid in ethanol and to this solution propylene glycol was added. To the obtained solution DHA was added and the mixture was left at room temperature for 3-4 days. Then DDW was added to the composition slowly under constant stirring. The composition was stirred for additional 15 minutes.

| | |
|---|---|
| DHA: | 23-350 mg |
| Phospholipid: | 70-250 mg |
| Ethanol: | 750-1050 mg |
| Propylene glycol: | 350-1000 mg |
| Water: | to 3.5 grams |

Example 8

Diazepam-Containing Composition 1 gram soy phospholipid was dissolved in a mixture of 3 grams ethanol and 9.8 grams propylene glycol and to this solution 400 mg of diazepam and 2.4 grams Labrasol were added. Water (3.4 grams) preheated to 40° C. was added slowly with constant stirring in Heidolph mixer (650 rpm). The composition was stirred for additional 15 minutes. The final composition contained 2% w/w diazepam.

Example 9

Granisetron HCl-Containing Composition 50 mg of soy phospholipids were dissolved in 150 mg ethanol. To this solution, 200 mg of propylene glycol and 10 mg labrasol were added and mixed. To the obtained mixture 15 mg of granisetron were added and dissolved. 575 microliter of DDW (at room temperature) were added very slowly under constant vortexing. The composition was stirred for additional 5 minutes.

Example 10

Granisetron HCl-Containing Composition 70 mg of Phospholipon 90 were dissolved in 150 mg ethanol. To this solution, 230 mg propylene glycol were added and mixed. To the obtained mixture, 20 mg of granisetron HCl were added and dissolved. 530 microliter of DDW (preheated to 40° C.) were added very slowly under constant vortexing. The composition was stirred for additional 15 minutes.

Example 11

Hypoglycemic Effect (Reduced Blood Glucose Levels) by Intranasal Administration of Insulin Tables IA and IB detail various compositions of human insulin, which were prepared according to the procedures described in Examples 1-6 above.

TABLE IA

| | % w/w | | | | | |
|---|---|---|---|---|---|---|
| Component | C | D | E | F | G | H |
| Insulin aqueous solution | 58 | — | 68.5 | 20 | 58 | 58 |
| Phospholipon 90 | 2 | 2 | 1.5 | 2 | — | 2 |
| Ethanol | 30 | 30 | 22.5 | 30 | — | 10 |
| Propylene Glycol | 10 | 10 | 7.5 | 10 | — | 10 |
| Water (double distilled) | — | 58 | — | 38 | 42 | 20 |
| Final insulin dose administered to mice IU/25 μL of composition | 1.45 | 0 | 1.71 | 0.5 | 1.45 | 1.45 |

| | % w/w | | | | | |
|---|---|---|---|---|---|---|
| Component | H | I | J | K | L | M |
| Insulin aqueous soln. | 58 | — | 58 | 58 | 58 | 58 |
| Phospholipon 90 | 2 | 2 | 1 | 0.25 | 0.5 | 5 |
| Ethanol | 12 | 12 | 15 | 15 | 15 | 12.5 |
| Propylene Glycol | 10 | 10 | 5 | 10 | 12 | 5 |
| Water (double distilled) | 18 | 76 | 21 | 16.75 | 14.5 | 19.5 |
| Final insulin dose administered to mice IU/25 μl of Composition | 1.45 | 0 | 1.45 | 1.45 | 1.45 | 1.45 |

TABLE IB

| | % w/w | | | | | | | | |
|---|---|---|---|---|---|---|---|---|---|
| Component | N | O | P | Q | R | S | T | U | V |
| Insulin aqueous soln. | 58 | 58 | 58 | 58 | 58 | 58 | 58 | 58 | 58 |
| Phospholipon 90 | 5 | 2 | 9 | 10 | 8 | 1 | 5 | 5 | 1 |
| Cholesterol | — | — | 1 | — | — | 0.1 | 1.5 | — | — |
| Ceramide | — | — | — | 1 | — | — | — | 0.2 | — |
| Tween 20 | — | — | — | 1.8 | — | — | 6.5 | — | — |
| Ethanol | 15 | 15 | 20 | 20 | 20 | 20 | 18.5 | 14.8 | 12 |
| Propylene Glycol | 10 | 10 | 12 | 9 | 10 | 10 | 10 | 10 | 15 |
| Water (double distilled) | 12 | 15 | — | — | 3.9 | 9.8 | — | 11.9 | 13.5 |
| Hydroxypropyl cellulose | — | — | — | 0.2 | 0.1 | — | — | — | 0.5 |
| Carbopol | — | — | — | — | — | 0.1 | 0.5 | 0.1 | — |

The effect of nasal administration of insulin to mice by means of the compositions described in Tables IA and IB was tested as follows.

Experiments were carried out on C75/b1 male mice (weight 22-28 g). 25 μL of the Compositions (see Figures and Table) were applied to the nasal cavity of the animal under short isofluran anesthesia. The mice have not received food during the experiment. Blood glucose levels were measured by glucose oxidase method using Glucometer Elite (disposable strips). The measurements were performed starting from one hour prior to intranasal administration of Compositions up to a maximum of 8 hours from the administration. Compositions D and I were used as Placebo controls for the Compositions C and H, respectively. Composition G served as the insulin aqueous solution control.

Figure 1:
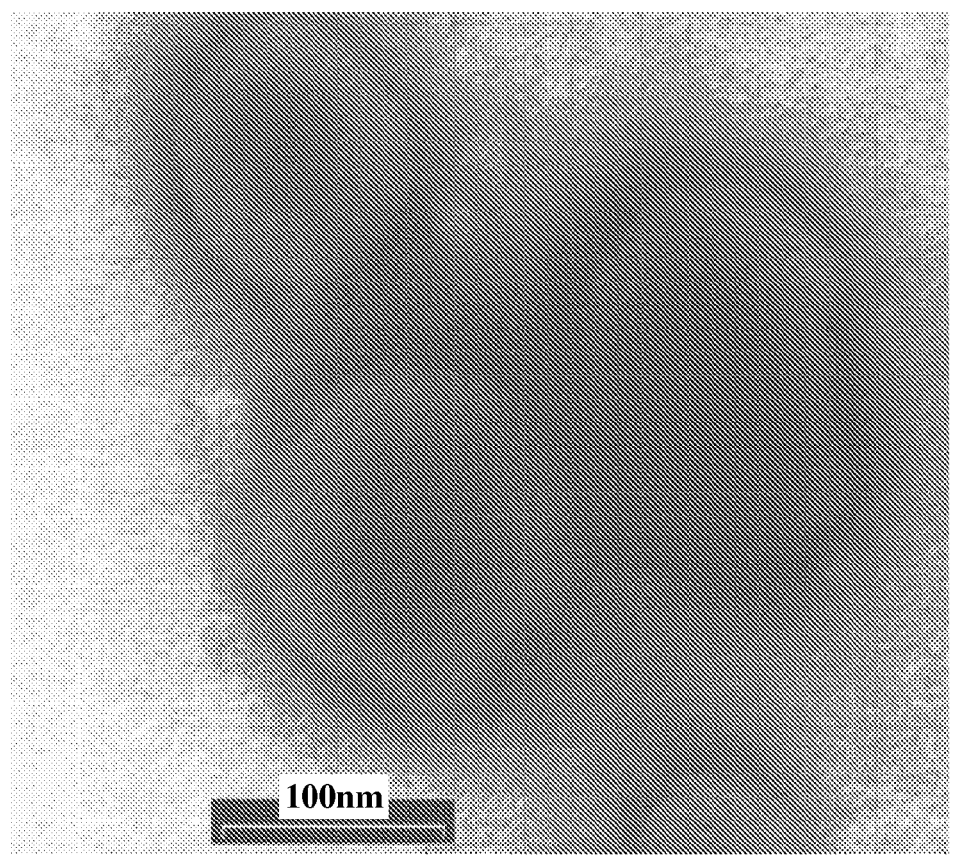
FIG. 1 is a TEM of insulin vesicles in a Composition F according to the invention.
Figure 2:
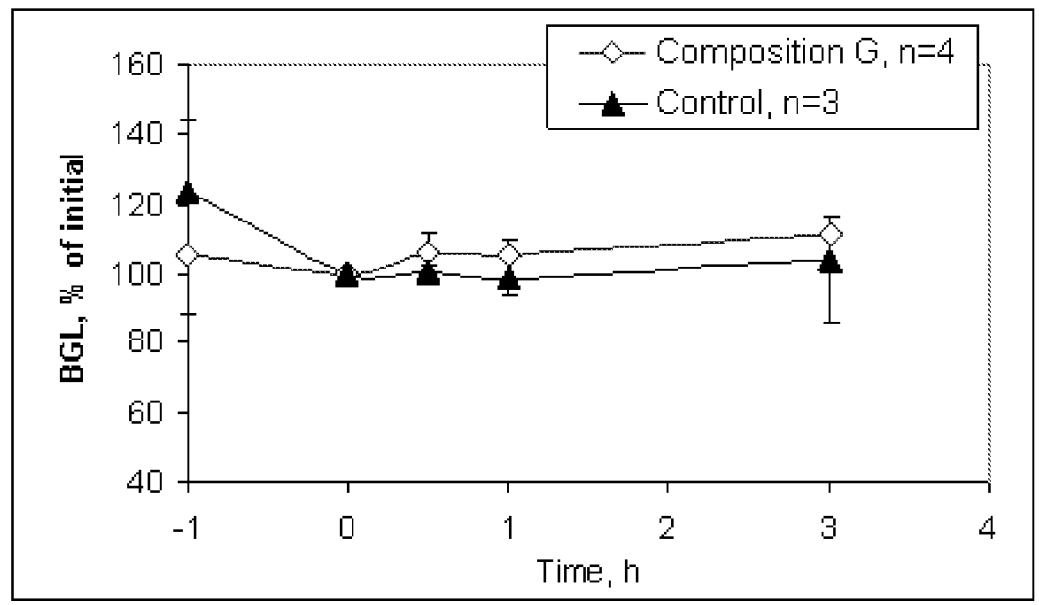
FIG. 2 is a graph showing blood glucose levels (% of initial) in mice following intranasal administration of 25 μL of insulin composition G (aqueous control containing 58 IU/ml), versus untreated mice.
Figure 3:
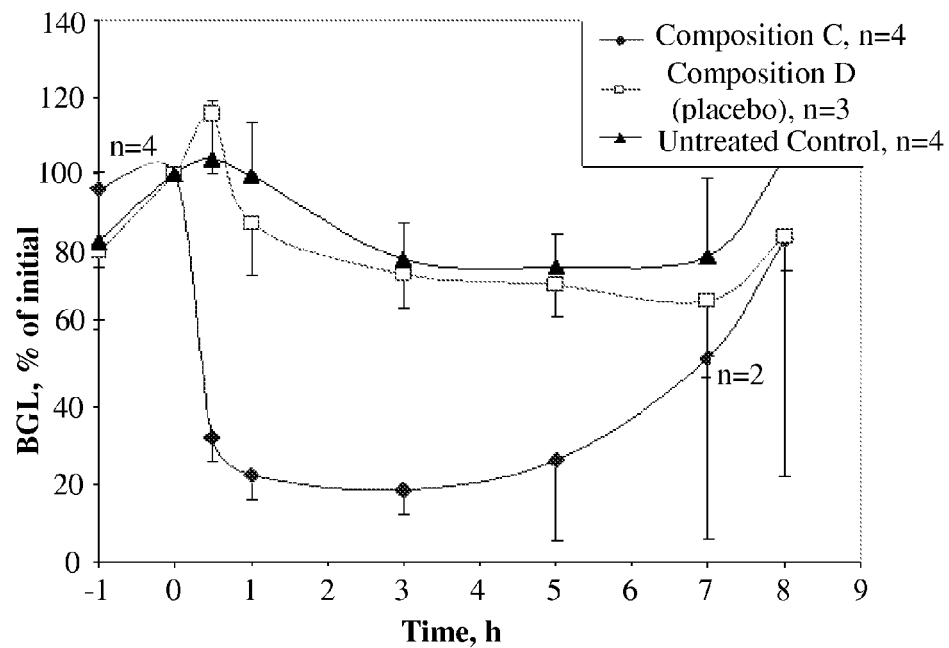
FIG. 3 is a graph showing blood glucose levels (% of initial) in mice following intranasal administration of 25 μL of human insulin compositions C (a composition of the invention containing 58 IU/ml insulin) and D (placebo), versus untreated mice.
Figure 4:
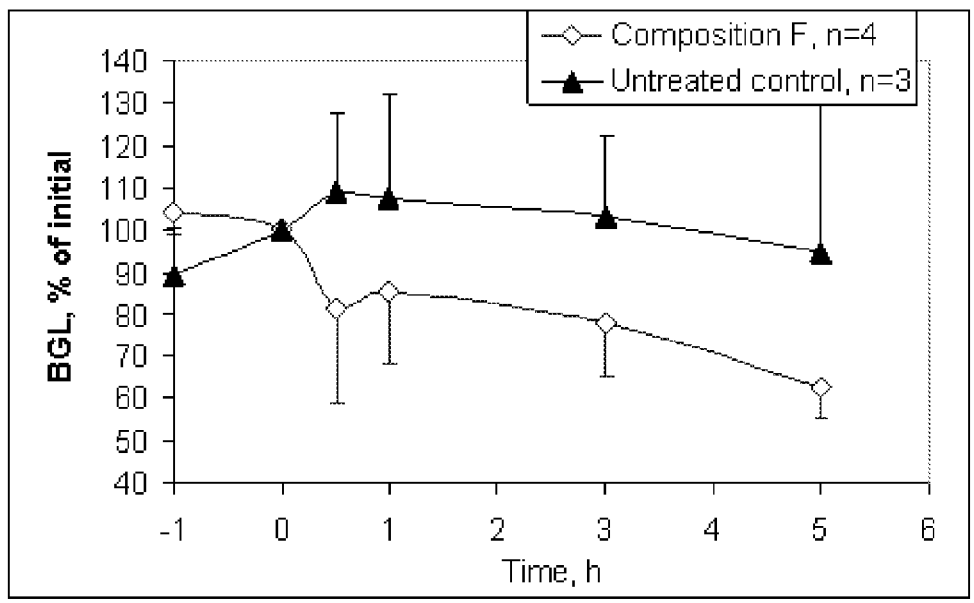
FIG. 4 is a graph showing blood glucose levels (% of initial) in mice following intranasal administration of 25 μL of insulin composition F (a composition of the invention containing 20 IU/ml insulin), versus untreated mice.
Figure 5:
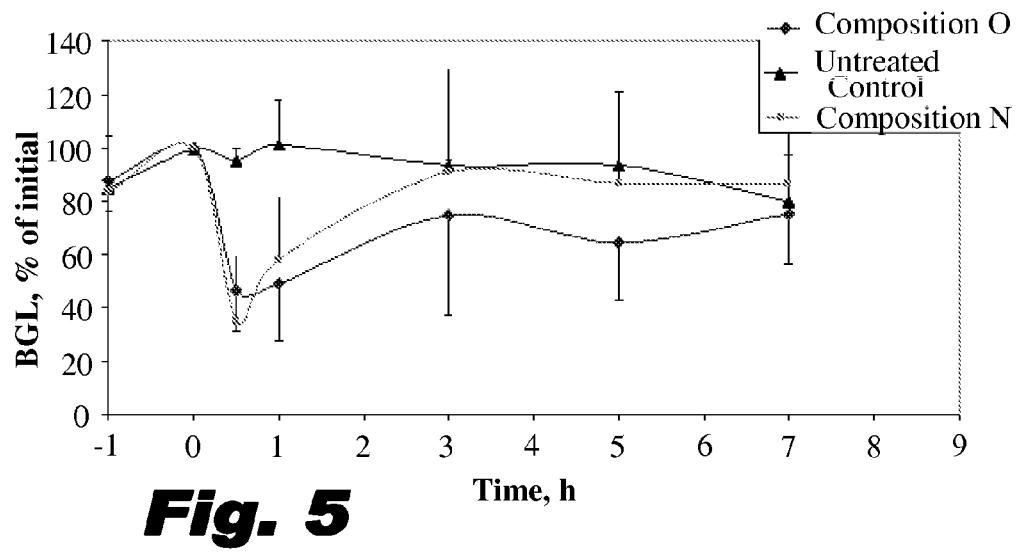
FIG. 5 is a graph showing blood glucose levels (% of initial) in mice following intranasal administration of 25 μL of insulin compositions N and O (compositions of the invention containing 58 IU/ml insulin) versus untreated mice.

FIGS. 2-5 present the Blood Glucose Levels (BGL) profiles following administration of various insulin compositions. Administration of compositions D and I (placebo controls), or composition G (aqueous control) had no effect on BGL (FIGS. 2 and 3). Compositions C, F, N and O significantly improved intranasal insulin absorption reducing the BGL.

Example 12

Treatment and Prophylaxis of Malaria by Intranasal Administration of Dihydroartemisinin (DHA)

Table II details compositions of dihydroartemisinin, which were prepared according to the procedure described in Example 7 above.

TABLE II

| | % w/w | | | | |
|---|---|---|---|---|---|
| Component | A | B | C | D | E |
| Dihydroartemisinin (DHA) | 0.66 | 0.66 | 0.33 | 0.40 | 10 |
| Phospholipon 90 | 2 | 2 | 5 | 2 | 5 |
| Ethanol | 27 | 20 | 17 | 22 | 28 |
| Propylene Glycol | 10 | 20 | 20 | 15 | 25 |
| Tween 20 | — | 10 | — | 5 | 2 |
| Water (double distilled) | 54.34 | 47.34 | 57.67 | 55.6 | 30 |

Example 13

Intranasal Administration of Diazepam

The efficacy of the intranasal administration of the diazepam-containing composition prepared according to Example 8 was tested by means of the following experiments.

Experiment 1:

The experiments were carried out on Female Balb/c mice (21-26 grams). Two experimental groups were used: control (untreated) (n=6) and treated group (n=6). The animals in active treatment group were administered with the Diazepam intranasal Phospholipid ethanolic vesicular compositions 2.9 μl in each nostril (5 mg/kg animal). Half an hour after nasal application, each animal in treated and control groups was intraperitoneally administered with acetic acid 0.6% (10 ml/kg) and individually housed in cage with a smooth flat floor. Antinociception effect was recorded by counting the number of writhes 5 minutes after injection of acetic acid for period of 10 minutes. A writhe is indicated by abdominal constriction and stretching of at least one hind limb.

Figure 6:
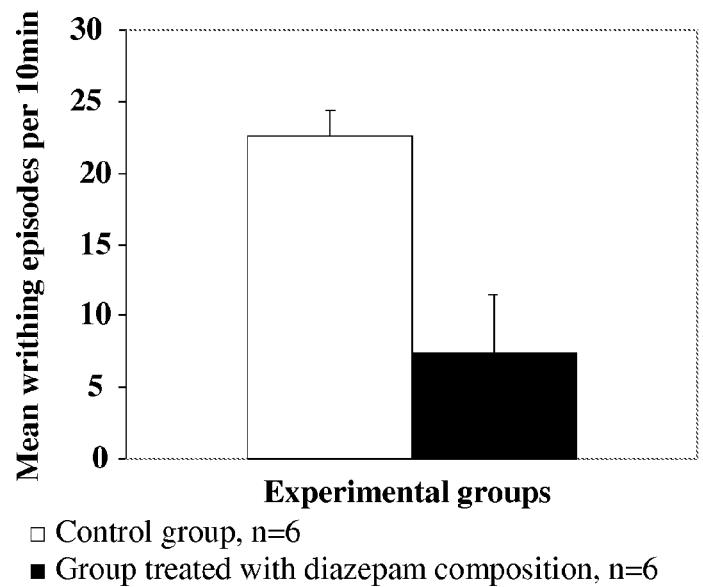
FIG. 6 is a bar diagram showing the results of a writhing test in mice following administration of diazepam vesicular composition prior to writhing induction with acetic acid, versus untreated control.

FIG. 6 is a bar diagram illustrating the results obtained, which show that intranasal administration of diazepam from the vesicular composition, 0.5 hour before acetic acid injection efficiently prevented writhing episodes.

Figure 7:
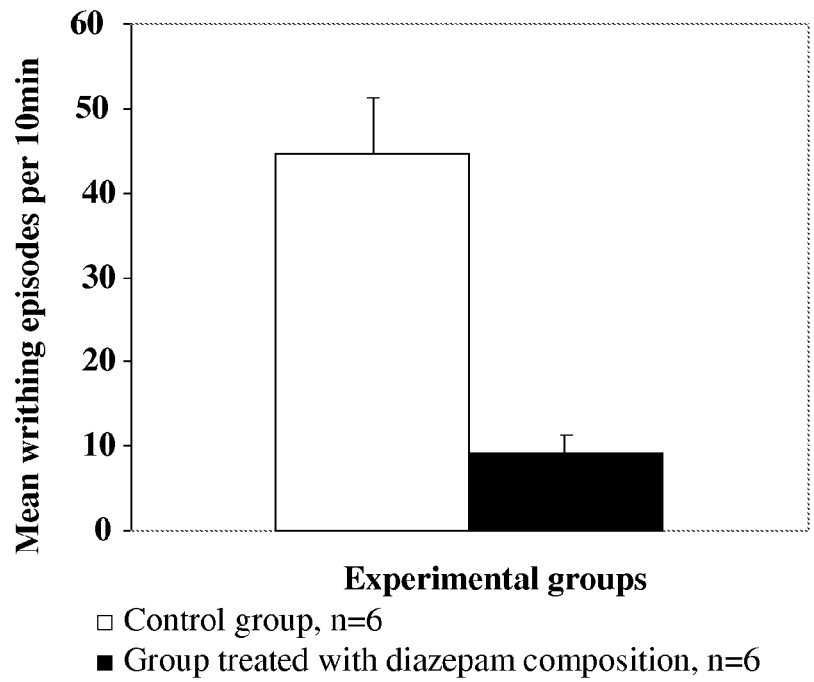
FIG. 7 is a bar diagram showing the results of a writhing test in mice following administration of diazepam vesicular carrier (drug dose 5 mg/kg) simultaneously with writhing induction with acetic acid solution, versus untreated control.

Experiment 2:

The experiment was carried out on Female Balb/c mice (21-26 grams). Two experimental groups were used: control (untreated) (n=6) and treated group (n=6). The animals in active treatment group were administered with the Diazepam intranasal vesicular composition 2.9 μl in each nostril (5 mg/kg animal). Immediately after nasal application (t=0), each animal in treated and control groups was intraperitoneally administered with acetic acid 0.6% (10 ml/kg) and individually housed in cage with a smooth flat floor. Antinociception was recorded by counting the number of writhes 5 minutes after injection of acetic acid for period of 10 minutes. FIG. 7 is a bar diagram illustrating the results obtained, which show that intranasal administration of diazepam from the vesicular composition simultaneously with injection of acetic acid solution was efficient in treating writhing episodes.

Experiment 3:

The experiments were carried out on Female Balb/c mice (21-26 grams). Three experimental groups were used: control (untreated) (n=4), mice intranasally administered with the diazepam IN vesicular composition (2.8 μl in each nostril=diazepam dose of 5 mg/kg animal) (n=4) and mice subcutaneously administered with the diazepam solution 0.125% at dose of 5 mg/kg animal (n=4). The animals in active treatment groups were administered with the Diazepam intranasal composition and subcutaneous diazepam. Simultaneously, each animal in treated and control groups was intraperitoneally administered with acetic acid 0.6% (10 ml/kg) and individually housed in cage with a smooth flat floor. Antinociception was recorded by counting the number of writhes 5 minutes after injection of acetic acid for period of 10 minutes.

Figure 8:
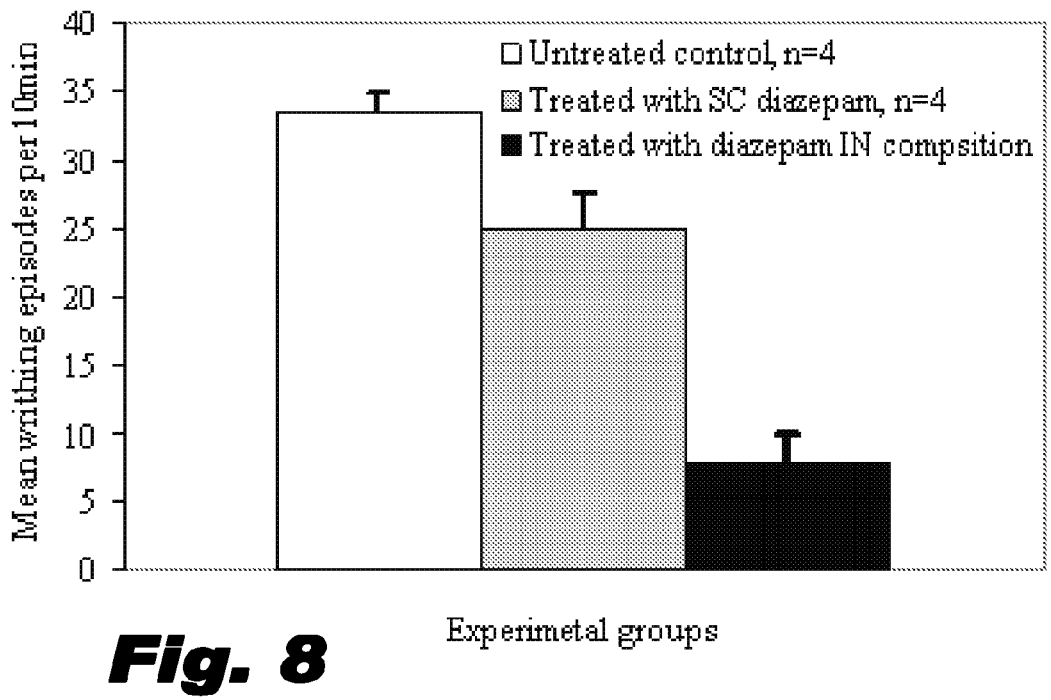
FIG. 8 is a bar diagram showing the results of a writhing test in mice following intranasal (IN) administration of diazepam phospholipid ethanolic vesicles composition (drug dose 5 mg/kg) and subcutaneous (SC) injection of diazepam simultaneously with writhing induction with acetic acid solution versus untreated control.

FIG. 8 is a bar diagram illustrating the results obtained, which show that intranasal administration of diazepam from the vesicular composition, was significantly more efficient in treating writhing episodes as compared to the same dose of the drug administered subcutaneously.

Example 14

Intranasal Administration of Granisetron HCl

Table III details compositions of granisetron, which were prepared according to the procedures described in Examples 9-10 above.

TABLE III

| | % w/w | | | | |
|---|---|---|---|---|---|
| Component | A | B | C | D | E |
| Granisetron HCL | 1.5 | 1.5 | 2 | 3 | 4 |
| Phospholipon 90 | 5 | 5 | 5 | 5 | 2 |
| Ethanol | 10 | 15 | 18 | 25 | 27 |
| Propylene Glycol | 20 | 20 | 12 | 5 | 20 |
| Labrasol | — | 1 | 1 | 1 | 1 |
| Water (DDW) | 63.5 | 57.5 | 62 | 61 | 46 |

| | % w/w | | | | |
|---|---|---|---|---|---|
| Component | F | G | H | I | J | K |
| Granisetron HCL | 5 | 1.5 | 2 | 1.5 | 2 | 1 |
| Phospholipon 90 | 5 | 0.5 | 7 | 10 | 5 | 5 |

TABLE III-continued

| | | | | | | |
|---|---|---|---|---|---|---|
| Ethanol | 10 | 10 | 15 | 12 | 10 | 10 |
| Propylene Glycol | 20 | 20 | 23 | 15 | 20 | 20 |
| Labrasol | 1 | 1 | — | 2 | 12 | 6 |
| Water (DDW) | 59 | 67 | 53 | 59.5 | 51 | 58 |

The compositions detailed in Table III were used for the intranasal administration of granisetron hydrochloride to rats and the pharmacodynamic response thereof was evaluated as follows.

Experiments were carried out on Male SD/H rats weighing 200-240 grams. The animals were housed individually in cages (23×23×20 cm) in a room with a 12-hour light/12-hour dark cycle (lights on between 06:00 and 18:00 hour) at a constant temperature (27±1° C.) and humidity (50±5%). Pelleted food and water was available ad libitum. Each cage had a wire-mesh floor to permit collection of spilt kaolin and food. Kaolin pellets were prepared according to the methods described Takeda et al. (1993). Briefly, gum Arabic and hydrated aluminum silicate (kaolin—China clay) were mixed together (1:100 on a weight: weight basis) with distilled water to form a thick paste. Pellets of the resulting kaolin mixture were shaped to resemble the dimensions of the rats' normal laboratory diet. The pellets were dried completely at room temperature.

The kaolin pellets were introduced into the cages 3 days prior to drug administration. They were held in identical stainless-steel containers (7×8×3 cm, attached to the side of the cage) to the food pellets. The kaolin and food containers were removed each day (at 10:00 a.m.) and the spilt kaolin and food collected, to determine the rats' consumption, during each 24-hour period, up to a total 72 hour observation time. Rat weight was also recorded on a daily basis.

Ipecac syrup 5 ml/kg was administrated orally and animals returned to the experiment cages. Rats were administrated with intranasal Granisetron HCl Composition B (at a dose of 1.5 mg granisetron HCl/kg rat). One hour after intranasal administration of granisetron, Ipecac syrup was given orally using a gavage to treated (n=5) and untreated (control, n=5) animals. Immediately after Ipecac syrup, the animals in the treatment group were administered with an additional dose of intranasal Granisetron hydrochloride followed by drug intranasal administration at regular 12-hour intervals for additional 2.5 days. Kaolin and food intake as well as rat weights were measured at 24, 48 and 72 hours post-Ipecac.

Figure 9:
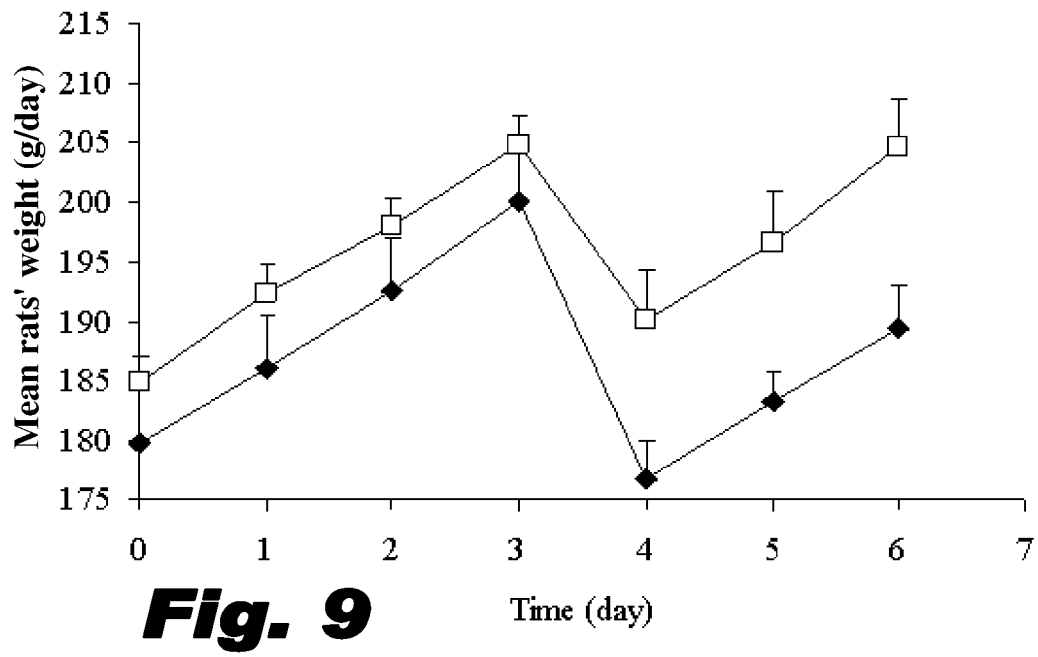
FIG. 9 is a graph depicting the changes in the weight of rats following administration of ipecac syrup and inducing Pica syndrome on day 3 in animals intranasally treated with granisetron HCl composition B (IN-GR, 1.5 mg drug/kg rat, n=5), versus untreated control (n=5)
Figure 10:
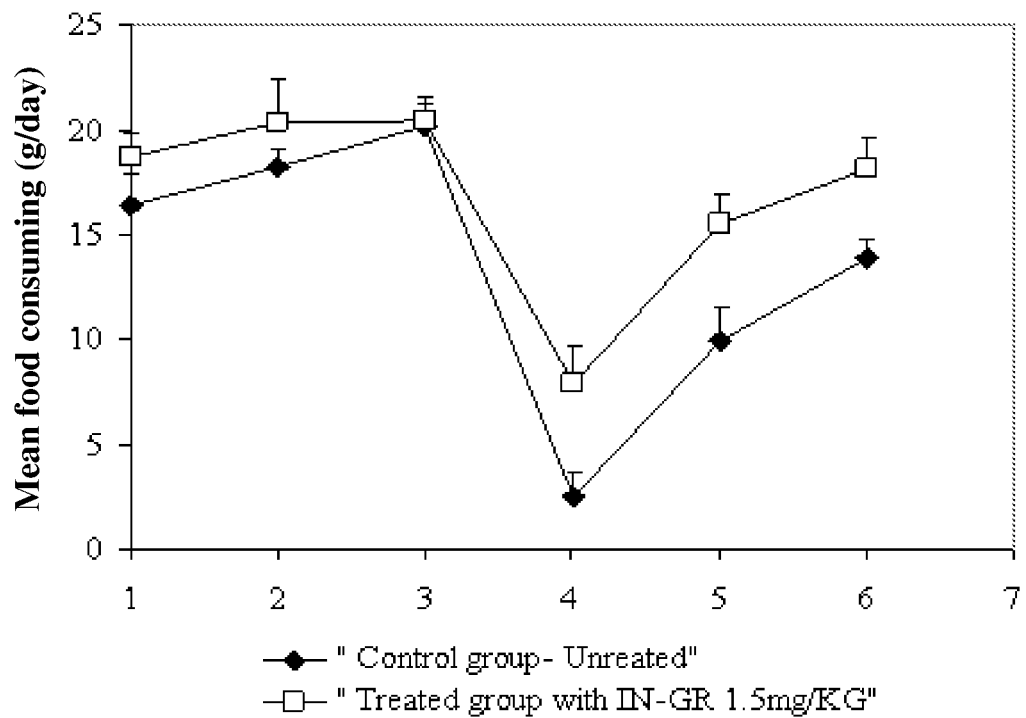
FIG. 10 is a graph showing the changes in the food consumption in rats following administration of ipecac syrup and inducing Pica syndrome on day 3 in animals intranasally treated with granisetron HCl Composition B (IN-GR, 1.5 mg drug/kg rat, n=5), versus untreated control (n=5)
Figure 11:
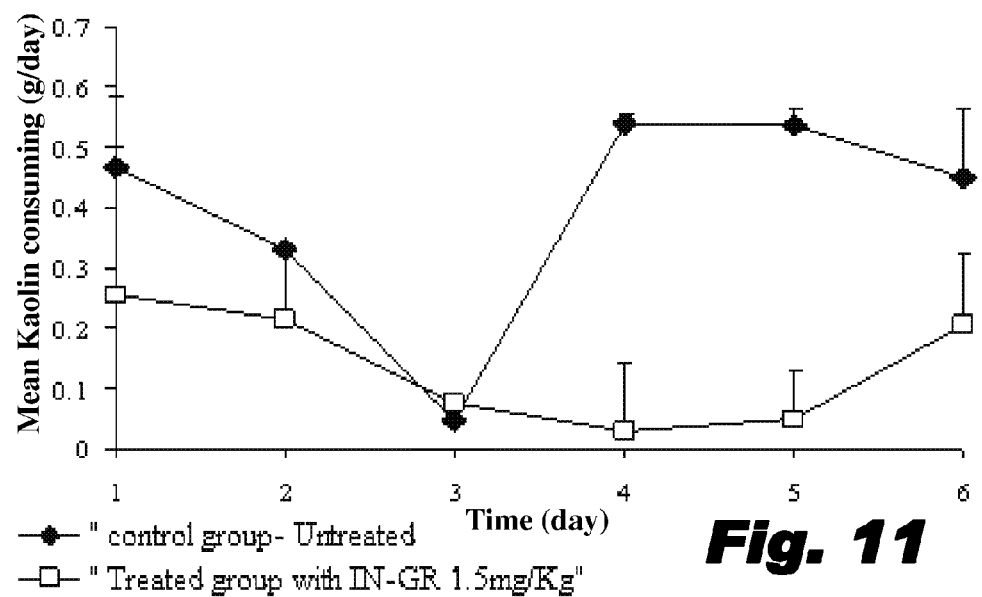
FIG. 11 is a graph showing the changes in the kaolin consumption in rats following administration of ipecac syrup and inducing Pica syndrome on day 3 in animals intranasally treated with granisetron HCl Composition B (IN-GR, 1.5 mg drug/kg rat, n=5) versus untreated control (n=5)

The results collected are represented in FIGS. 9 to 11. The Results show that intranasal administration of granisetron HCl from composition B, was efficient in preventing weight loss (FIG. 9), stimulating food consumption (FIG. 10) and preventing kaolin consumption (FIG. 11) in rats with Pica syndrome (equivalent to emesis and vomiting in humans).

Example 15

Transport of Fluorescent Probe Across Nasal Mucosa Following In Vivo Administration Visualization of rhodamine B (hydrophilic probe, MW 479) permeation across the nasal mucosa using the composition of the invention (containing 0.05% (0.5 mg/mL) Rhodamine B) was carried out as follows.

A stock solution of rhodamine B (2 mg/mL) was prepared in water. 50 mg of phospholipid were dissolved in 200 mg ethanol. To this solution 100 mg propylene glycol and 10 mg labrasol were added and mixed. To the obtained mixture 250 microliter of the aforementioned aqueous rhodamine B solution (2 mg/ml) were added slowly with constant stirring. The residual 390 microliter of DDW were added slowly to the obtained system with constant vortexing. The composition was stirred for additional 5 minutes. The composition is described in Table IV.

TABLE IV

| Component | % w/w |
|---|---|
| Rhodamine B stock aqueous soln. | 25 |
| Phospholipon 90 | 5 |
| Ethanol | 20 |
| Propylene Glycol | 10 |
| Labrasol | 1 |
| Water (DDW) | 39 |

The composition was applied intranasally to the right nostril of SD/H male 220-250 gram rats (application volume 100 μL) anesthetized intraperitoneally with Ketamine-Xylazine mixture The animals were sacrificed 0.5 hour from the application and the nasal septum with the adjunct epithelial membrane from each animal were carefully removed from the bone. The harvested septum was fixed with 3.8% Formalin in PBS (pH 7.4) for 1 hour in room temperature. The untreated epithelia on the left side of the septum were separated from the septum. The septum with right side epithelia was placed on the slide, covered with cover glass, fixed with tape and observed under CLS microscope (10-40×/0.6 plan Neofluor lens, Zeiss LSM 410 confocal system with an Axiovert 135 inverted microscope).

Figure 12:
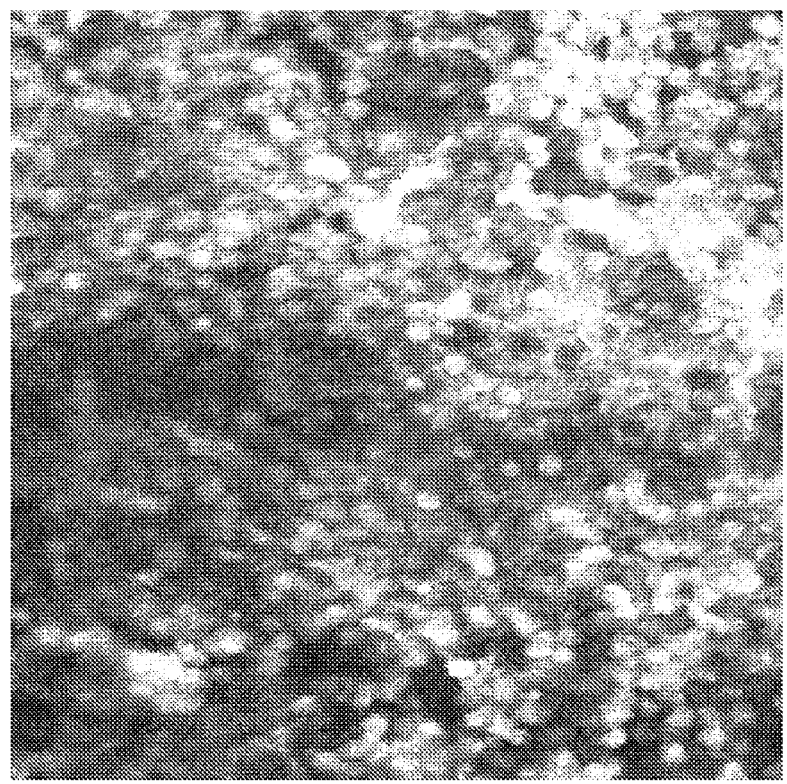
FIG. 12 is a confocal laser scanning (CLS) micrograph showing the transport of Rhodamine B across the nasal mucosa from the composition of the invention applied for 0.5 hour to the rat nostril, whereas white is the highest fluorescent intensity.

FIG. 12 is a photograph showing that the composition of the invention efficiently delivered rhodamine B across the nasal mucosa (White means the highest fluorescent intensity).

Example 16

Granisetron HCL-Containing Composition in the Form of a Viscous Liquid 700 mg of Phospholipon 90 were dissolved in 1500 mg ethanol. To this solution 2300 mg of propylene glycol were added and mixed. To the obtained mixture 200 mg of granisetron were added and dissolved. 5280 microliter of DDW (preheated to 40° C.) were added very slowly under constant mixing in Heidolph mixer (650 rpm). The composition was mixed for additional 15 minutes. To the obtained system 20 mg of hydroxypropylcellulose were added slowly and mixed for additional 15 minutes in Heidolph mixer (650 rpm). The resulting composition was left for 30 minutes in room temperature and then mixed for additional 5 minutes.

Example 17

Insulin-Containing Composition in the Form of a Semi-Solid 0.2 grams of phospholipon 90 were dissolved in 3 grams ethanol and to this solution 0.94 grams propylene glycol were added. The obtained solution was added slowly to 5.8 mL of the aqueous insulin solution (100 IU/mL) under constant stirring at room temperature in Heidolph mixer (650 rpm). The composition was stirred for additional 5 minutes. To the obtained system 60 mg of hydroxypropylcellulose were added slowly and mixed for additional 15 minutes in Heidolph mixer (650 rpm). The resulting composition was left for 30 minutes in room temperature and then mixed for additional 10 minutes. The final semi-solid composition contains 58 IU insulin/gram.

Example 18

Insulin-Containing Composition in the Form of a Gel 0.2 grams of Carbopol 980 were dispersed in 2.48 grams DDW in Heidolph mixer (400 rpm) followed by a slow addition of 0.2 grams of TEA. The mixture was left for 10 minutes in room temperature to obtain the gel phase.

In another container 0.2 grams of Phospholipin 90 were dissolved in 2 g EtOH to this solution 1 gram of propylene glycol and 0.02 grams of Vitamin E were added and mixed to obtain clear system in Heidolph mixer (700 rpm). The obtained system was stirred for additional 5 minutes and added slowly to the gel phase under constant mixing at 400 rpm. To the obtained semi-solid preparation 3.9 mL of insulin aqueous solution containing 250 IU/mL (prepared from dissolving 40.6 mg of human insulin powder containing 24 IU/mg (Sigma) in DDW was added. The obtained composition was mixed for additional 5 minutes. It is notable that insulin solution could be added in each stage of the preparation. The final semi-solid composition contained 97.5 IU insulin/gram.

Example 19 (Comparative)

Insulin-containing compositions were prepared, as described in Table V below:

TABLE V

| | Compositions,, % w/w | | |
|---|---|---|---|
| Component | I | II | III |
| Insulin aqueous solution 100 IU/ml | 63 | 63 | 63 |
| Phospholipon 90 | 2 | 2 | 2 |
| Ethanol | 25 | 10 | 2 |
| Propylene Glycol | 10 | — | — |
| DDW | — | 25 | 33 |
| Final insulin dose administered to mice IU/25 µL of Composition | 1.575 IU | 1.575 IU | 1.575 IU |

Experimental Protocol:

Nasal absorption experiments with insulin compositions I, II (control composition containing 10% EtOH) and III (control liposomal composition containing 2% EtOH) were performed in ICR/male mice (7-10 weeks) obtained from (Harlan/Israel). The animals were fasted 1 hour prior to an insulin administration and during the experiment time, with free access to water. Compositions were intranasally administered to the animals (12.5 µl in each nostril, a total of 25 µl per animal—each nose side), using a pipette with a disposable plastic tip. The nasal insulin formulations were administered immediately following a short isofluran anesthesia. The total amount of insulin delivered nasally to each animal, was 1.575 IU. Blood glucose levels were measured by glucose oxidase method using Glucometer Elite (disposable strips). The measurements were performed starting from one hour prior to intranasal administration of compositions up to 6 hours from the administration.

The results presented in FIG. 13 show that composition I efficiently reduced blood glucose levels, while administration of compositions II and III (controls) had no effect on BGL.

Example 20

Buspirone HCl-Containing Composition

The following compositions were prepared:

| | % w/w | |
|---|---|---|
| Component | A | B |
| Buspirone HCL | 1 | 2 |
| Phospholipon 90 | 2 | 2 |
| Ethanol | 20 | 25 |
| Propylene Glycol | 10 | — |
| Vitamin E | 0.2 | 0.2 |
| Carbopol 980 | 1 | — |
| Triethanolamine (TEA) | 1 | — |
| Water (DDW) | 64.8 | 70.8 |

Preparation Method for Buspirone Composition A:

0.1 grams of Carbopol 980 was dispersed in 2.48 grams DDW in Heidolph mixer (400 rpm) to this dispersion 1 gram of EtOH was added under constant mixing followed by a slow addition of 0.1 gram of TEA. The mixture was left for 10 minutes at room temperature to obtain the gel phase.

In another container 0.2 grams of Phospholipin 90 were dissolved in I gram EtOH to this solution 1 gram of propylene glycol and 0.02 grams of Vitamin E were added and mixed to obtain a clear system. To this system 0.1 grams of buspirone HCl dissolved in 4 grams DDW were slowly added under constant stirring at room temperature in Heidolph mixer (700 rpm). The obtained system was stirred for additional 5 minutes and added slowly to the gel phase under constant mixing at 400 rpm. The obtained composition A was mixed for additional 5 minutes.

Preparation Method for Buspirone Composition A:

0.2 grams of Phospholipin 90 were dissolved in 2.5 grams EtOH; to this solution 0.02 grams of Vitamin E were added and mixed to obtain a clear system. To this system, 0.2 grams of buspirone HCl dissolved in 7.08 grams DDW were slowly added under constant stirring at room temperature in Heidolph mixer (700 rpm). The obtained system was stirred for additional 5 minutes.

Example 21

Insulin-Containing Composition 0.2 grams of phospholipids (Phospholipon 90) were dissolved in 1.5 grams ethanol and to this solution 0.5 grams propylene glycol were added.

Insulin aqueous solution containing 250 IU/mL insulin was prepared by dissolving 81.25 mg of human insulin powder containing 24 IU/mg (Sigma) in 7.8 mL DDW. The obtained insulin aqueous solution was added slowly under constant stirring at room temperature to the previously prepared phospholipid solution. The composition is stirred for additional 5 minutes. The final composition contains 195 IU insulin/g.

Example 22

Glatiramer Acetate-Containing Composition

The following compositions were prepared:

| Component | % w/w | | |
|---|---|---|---|
| | A | B | C |
| Glatiramer acetate | 1 | 2 | 2 |
| Soy phospholipids | 2 | 2 | 3 |
| Ethanol | 20 | 25 | 15 |
| Propylene Glycol | 10 | — | 10 |
| Vitamin E | 0.2 | 0.2 | 0.2 |
| Carbopol 980 | 1 | — | 0.1 |
| Triethanolamine (TEA) | 1 | — | 0.1 |
| Water (DDW) | 64.8 | 70.8 | 69.6 |

Example 23

Paroxetine-Containing Composition

The following compositions were prepared:

| Component | % w/w | |
|---|---|---|
| | A | B |
| Paroxetine | 0.5 | 1 |
| Phosphatydylcholine | 2.5 | 3 |
| Ethanol | 23 | 15 |
| Propylene Glycol | 10 | 15 |
| Vitamin E | 0.2 | 0.2 |
| Labrasol | 1 | — |
| Water (DDW) | 62.8 | 65.8 |

Example 24

Rivastigmine-Containing Composition

The following compositions were prepared:

| Component, % w/w | A | B |
|---|---|---|
| Rivastigmine tartrate | 0.5 | 0.75 |
| Soy Phospholipid | 2 | 5 |
| Ethanol | 12 | 20 |
| Propylene Glycol | 10 | 15 |
| Water (DDW) | 75.5 | 59.25 |

Example 25

Sibutramine-Containing Composition

The following compositions were prepared:

| Component | % w/w | |
|---|---|---|
| | A | B |
| Sibutramine | 1 | 1.5 |
| Phospholipon 90 | 5 | 2 |
| Ethanol | 14 | 22 |
| Propylene Glycol | 15 | — |
| Vitamin E | 0.2 | — |
| Labrasol | 1 | — |
| Water (DDW) | 63.8 | 74.5 |

Pain Treatment with Nasal Compositions

Example 26

Tramadol (Pain Treatment) Nasal Composition

| Component | % w/w |
|---|---|
| Tramadol HCl | 0.9 |
| Phospholipid | 5 |
| Ethanol | 15 |
| Propylene Glycol | 20 |
| Vitamin E | 0.2 |
| Water (DDW) | 59.1 |

10 grams of the above formulation were prepared as follows: 0.5 g soy phospholipid was dissolved in 1.5 grams ethanol and 2 grams propylene glycol was added to this solution followed by addition of Vitamin E and mixing for 5 minutes. Then, 90 mg Tramadol HCl was added to this mixture. Water was added slowly with constant stirring by a Heidolph overhead stirrer. The composition is stirred for additional 10 minutes. The final composition contains 9 mg/g Tramadol HCl.

Example 27

Tramadol (Pain Treatment) Nasal Composition

| Component | % w/w |
|---|---|
| Tramadol HCl | 4-20 |
| Phospholipid | 5 |
| Ethanol | 15 |
| Propylene Glycol | 22 |
| Vitamin E | 0.2 |
| Water (DDW) | to 100 |

The composition is prepared by the method described in Example 26. The final composition contains 10-50 mg/250 mg Tramadol HCl.

Regime for use in humans: 250 μL of the composition (125 μL in each nostril) as needed (up to 5 times/day)

Tramadol doses in humans: 20-250 mg once to up to 5 times daily

Administration modes: drops, spray, with a nebulizer or a device.

Example 28

Diazepam Nasal Composition

Higher Dose

| Component | % |
|---|---|
| Diazepam | 0.625 |
| Phospholipid | 2 |
| Ethanol | 15 |
| Propylene Glycol | 22 |
| Vitamin E | 0.2 |
| Water (DDW) | to 100 |

The above formulation was prepared as follows: phospholipid was dissolved in ethanol and propylene glycol was added to this solution followed by addition of Vitamin E and mixing. Then, Diazepam was added to this mixture. Water was added slowly with constant stirring by a Heidolph overhead stirrer. The composition is stirred for additional 15 minutes. The final composition contains 6.25 mg/mL Diazepam.

Example 29

Diazepam Nasal Composition

Lower Dose

| Component | % w/w |
|---|---|
| Diazepam | 0.3125 |
| Phospholipid | 2 |
| Ethanol | 15 |
| Propylene Glycol | 22 |
| Vitamin E | 0.2 |
| Water (DDW) | to 100 |

The composition was prepared as described above.

Example 30

Analgesic Effects of Nasal Tramadol Compositions in Mice

The analgesic efficacy of the intranasal administration of the tramadol-containing composition (composition detailed in Example 26) was tested.

The experiments were carried out on female C75/BL mice (8-9 weeks).

Fifteen mice were divided in three experimental groups of 5 animals, each:

Group 1: Intranasal administration of Tramadol HCl composition of Example 26 at a dose of 5 mg/Kg animal (0.09 mg/10 µl/mouse). 5 µl of the Composition were administered in each nostril.

Group 2: Oral administration of Tramadol HCl aqueous solution at a dose of 5 mg/kg animal (90 µg/100 µl per mouse).

Group 3: Untreated control animals.

Intraperitoneal injection of a weak solution of acetic acid induces a nociceptive stereotyped behavior (writhing) that mimics acute pain. This model is widely used to evaluate the analgesic (antinociceptive) effects of anti pain drugs.

The mice received treatment under Isoflurane® anesthesia. Half an hour after the treatment, all the mice in the two treatment groups and in the control group were intraperitoneally administered with acetic acid 0.6% (10 ml/kg) and individually housed in cages with a smooth flat floor.

Antinociception effect was recorded by counting the number of writhes 5 minutes after the injection of acetic acid for a period of 10 minutes. A writhe is indicated by abdominal constriction and stretching of at least one hind limb.

The results presented in FIG. 14 illustrate that intranasal administration of Tramadol HCl from the Composition of the invention, significantly diminished writhing episodes relative to oral administration of the same dose of drug or relative to control.

Example 31

Analgesic Effect of Diazepam in Mice Following Nasal Administration of the Compositions of the Invention Detailed in Examples 28-29

The analgesic efficacy of the intranasal administration of the Diazepam-containing composition (compositions detailed in Examples 28 and 29) was tested.

The experiments were carried out on female C75/BL mice (8-9 weeks).

Mice were divided in three experimental groups:

Group 1: Intranasal administration of Diazepam composition of Example 28 at a dose of 5 mg/Kg animal (0.125 mg/20 µl/mouse). 10 µl of the Composition were administered in each nostril.

Group 2: Intranasal administration of Diazepam composition of Example 29 at a dose of 2.5 mg/Kg animal (0.0625 mg/20 µl/mouse). 10 µl of the Composition were administered in each nostril.

Group 3: Untreated control animals.

The experiments were run accordingly to the protocol described in Example 30.

The results presented in FIG. 15 illustrate that intranasal administration of Diazepam at two doses from the Composition of the invention, significantly diminished writhing episodes relative to oral administration of the same dose of drug or relative to control. The obtained response is dose-dependant.

Example 32

Brotizolam (Hypnotic/Sleep Effect) Nasal Composition

| Component, | mg |
|---|---|
| Brotizolam | 0.25 |
| Phospholipid | 20 |
| Ethanol | 150 |
| Propylene Glycol | 200 |
| Vitamin E | 2 |
| Water (DDW) | To 1 ml |

The formulation was prepared according to the methods described above. Final formulation contains 0.25 mg/g Brotizolam.

Doses of Brotizolam in humans: 0.01 to about 1 mg preferably from about 0.05 to about 0.3 mg for one administration before sleep.

Example 33

Diphenhydramine Hydrochloride Nasal Composition

| Component | % w/w |
| --- | --- |
| Diphenhydramine Hydrochloride | 2-25 |
| Soy phospholipid | 5 |
| Ethanol | 12 |
| Propylene Glycol | 15 |
| Vitamin E | 0.2 |
| Water (DDW) | to 100 |

Soy Lecithin was dissolved in ethanol and propylene glycol was added to this solution. Tocopheryl acetate (Vit E) was added to the obtained mixture and mixed slowly for 15 minutes Diphenhydramine Hydrochloride was dissolved in water and this was added to the above mixture slowly and under constant stirring in Heidolph mixer. The composition is stirred for additional 15 minutes. The final composition contains 50-150 mg/mL Diphenhydramine HCl.

Administration as drops, spray, with a nebulizer or a device.

Regime and dosage for humans: 10-30 mg/200 µL (100 µL in each nostril) before sleep.

Example 34

Hypnotic (Sleep) Effect of Brotizolam in Mice Following Nasal Administration of the Composition of the Invention Test of Composition of Example 32

The efficacy of the intranasal administration of the above brotizolam-containing compositions was tested by means of the following experimental protocol using the assessment of pentobarbitone-induced sleeping in mice. In this test described below, the time in minutes, after treatment with pentobarbitone and loss of righting reflex was taken as sleep latency, whilst the time between loss of righting reflex and the regain of right reflex was taken as the duration of sleep. The model is widely used in rats and mice to evaluate the hypnotic/sedative effects of drugs [Avoka et al., J. Ethnopharmacol. 2006; 103:166-75].

Experimental Protocol:

The experiments were carried out on Female C57Bl/6 mice, 6-7 weeks old.

The following groups of animals were used (n=4):

Group 1: Intranasal administration of Brotizolam composition at a dose of 0.25 mg/Kg animal (18 µl/mouse). 9 µl of the Composition from Example 32 were administered in each nostril.

Group 2: Oral administration of Brotizolam at a dose of 0.25 mg/kg animal (18 µl/mouse).

Group 2: Untreated control animals given orally with water.

The animals were administered with the above compositions and 5 minutes later injected with Sodium Phenobarbital-SP (40 mg/kg i.p). The onset of the loss of righting reflex and the duration of the loss of the righting reflex were recorded as latency and total sleeping time in minutes (TST), respectively.

Figure 16:
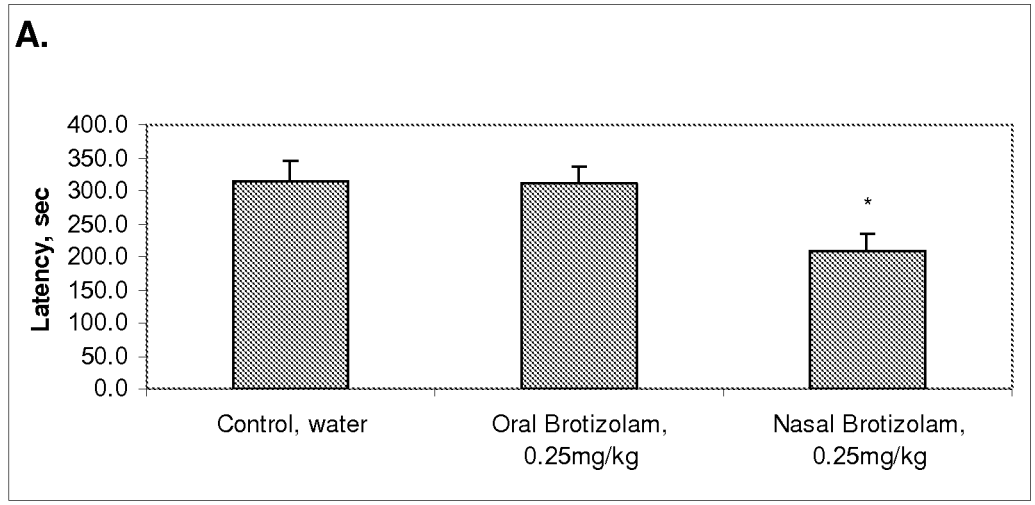
Figure 16:
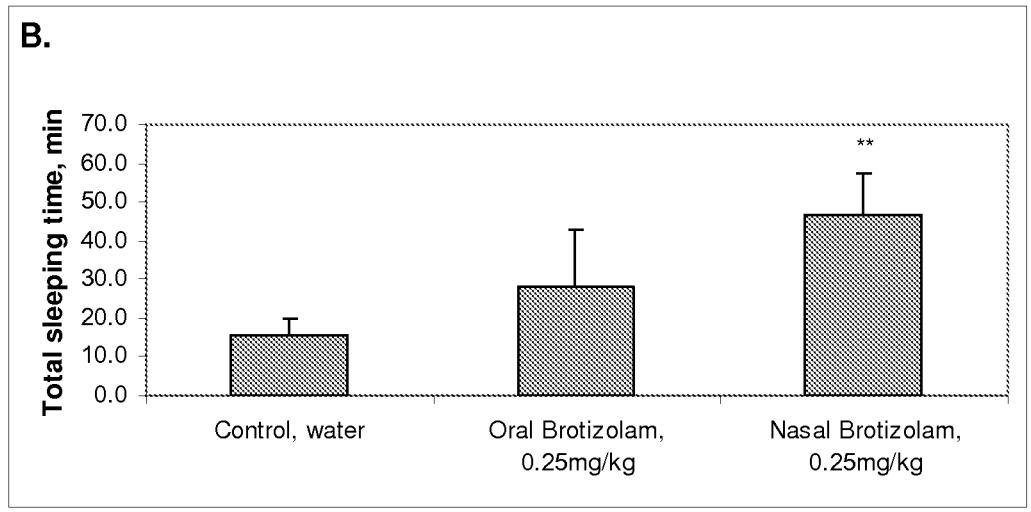

FIG. 16 presents the results of this experiment. It appears that nasal treatment with Brotizolam given only 5 minutes prior pentobarbitone administration significantly shortened the latency and significantly enhanced TST of pentobarbitone induced sleep. Oral Brotizolam had no significant effect on both parameters as compared to control.

Formulations for Treatment and Prophylaxis of Multiple Sclerosis

The efficiency of the nasal carrier of the invention is shown in the use of formulations for prophylaxis and treatment of neurological symptoms developed in an Experimental Allergic Encephalomyelitis (EAE) model (an animal model for multiple sclerosis)

Prophylaxis of Multiple Sclerosis

Example 35

Nasal Composition of the Invention Containing Corticosteroids

| Component, | % w/w |
| --- | --- |
| Prednisolone | 0.25 |
| Soy phospholipid | 5 |
| Ethanol | 15 |
| Propylene Glycol | 20 |
| Vitamin E | 0.2 |
| Water (DDW) | to 100 |

The composition was prepared by the methods described in previous examples. The final composition contains 2.5 mg/mL prednisolone.

Example 36

Prednisolone Solution for Subcutaneous (SC) Administration

Control Solution

| Component, % w/w | |
| --- | --- |
| PEG400 | 30 |
| Prednisolone | 0.05 |
| Normal saline | 69.95 |

Prednisolone was dissolved in the mixture of PEG400 and saline. A clear solution containing 0.5 mg/mL prednisolone was obtained.

Example 37

Effect of Corticosteroid Nasal Formulation on Prevention of EAE

EAE in mice is an accepted model of Multiple Sclerosis in humans.

Induction of EAE:

EAE was induced in female C57Bl/6 mice, 6-7 weeks old (weighting 17-18 g) using a slightly modified previously published protocol [Kataoka H, et al. Cell Mol. Immunol. 2005]. By using this procedure, the mice were immunized with Myelinoligodendrocyte glycoprotein ($MOG_{35-55}$) peptide mixed with mycobacteria in Complete Freund's adjuvant (CFA), followed by immediate and 48 hours later injections of Pertussis toxin.

Clinical assessment is performed on the basis of the following EAE score scale.

| Score | Signs | Description |
|---|---|---|
| 0 | Normal behavior | No neurological signs |
| 0.5 | Distal limb tail | The distal tail is limp and droops wobbly |
| 1 | Limb tail | The tail is limp and droops wobbly |
| 2 | Wright reflex | |
| 3 | Ataxia | Walk when the hinds legs are unsteady |
| 4 | Early paralysis | The rat/mouse has difficulties standing on his legs but still has remnants of movements |
| 5 | Full paralysis | The rat/mouse can't move its legs at all, it looks |
| 6 | Moribund-death | thinner and emaciated. Incontinence |

The following experimental groups were used, each containing 6 animals:

Group 1: Prophylactic intranasal administration of Prednisolone composition (Example 35) at a dose of 3 mg/Kg animal (0.05 mg/20 μl/mouse). 10 μl of the Composition were administered in each nostril twice daily, from $1^{st}$ to $4^{th}$ day after EAE induction, and then 1.5 mg/kg once a day (0.025 mg/10 μl per mouse, 5 μl/norise) until the end of the experiment.

Group 2: Prophylactic subcutaneous administration: Prednisolone 3 mg/kg (0.05 mg/100 μg per mouse), administrated as a control subcutaneously in solution of Example 36. The solution was injected subcutaneously twice daily, from $1^{st}$ to $4^{th}$ day after EAE induction, and then 1.5 mg/kg was administered once a day SC (0.025 mg/50 ul per mouse) until the end of the experiment.

Group 3: Control: no treatment.

The results presented in FIG. 17 show that intranasal administration of the Composition of the invention containing Prednisolone (Example 35) efficiently prevented the development of EAE as compared to SC administration of the same drug dose in solution.

Treatment of Multiple Sclerosis

Example 38

Nasal Composition of the Invention Containing Corticosteroids

| Component, % w/w | |
|---|---|
| Prednisolone | 0.5 |
| Phospholipid | 5 |
| Ethanol | 15 |
| Propylene Glycol | 20 |
| Vitamin E | 0.2 |
| Water (DDW) | 59.3 |

The composition was prepared by the methods described in previous examples. The final composition contains 5 mg/mL prednisolone.

Example 39

Nasal Composition of the Invention Containing Glatiramer Acetate (GA)

| Component, % w/w | |
|---|---|
| Phospholipid | 5 |
| Ethanol | 15 |
| Propylene Glycol | 20 |
| Vitamin E | 0.2 |
| GA aqueous solution for injection | to 100 |

The composition was prepared by the methods described in previous examples. The final composition contains 12 mg/mL GA.

Example 40

GA Solution for Subcutaneous (SC) Administration

Control Solution

| Component | |
|---|---|
| Copaxone® injection (20 mg/mL) | 180 μl |
| Normal saline to | 3000 μl |

Example 41

GA Solution for Nasal Administration

Control Solution

| Component | |
|---|---|
| Copaxone® injection (20 mg/mL) | 600 μl |
| Distilled water | 400 μl |

Example 42

Nasal Composition of the Invention Containing GA

| Component, % w/w | |
|---|---|
| GA | 1-10 |
| Phospholipid | 0.2-10 |
| Ethanol | 12-18 |
| Propylene Glycol | 5-25 |
| Tocopherol acetate or succinate | 0.2-0.5 |
| Water/Saline/Buffer | To 100 |

The composition was prepared by the methods described in previous examples. GA is added as an aqueous solution.

The GA solution could contain buffers, glycols, polyglycols, solubilyzers such as citrate esters, carbohydrates, mannitol, sugar alcohols, salts, stabilizers, antioxidants (BHA, BJT, sulfides, tocopherols, ascorbic acid derivatives).

The nasal composition contains 10-100 mg/mL GA.

The compositions could be administered as drops, nebulation, spray, device, special device for nasal delivery to brain.

Dosage in humans: 5-80 mg GA administered as needed.

Administration of the nasal composition could be made every day or every other day or once a week.

Example 43

Nasal Composition of the Invention Containing Corticosteroids

| Component | % w/w |
|---|---|
| Prednisolone | 1-12 |
| Phospholipid | 1-5 |
| Ethanol | 12-20 |
| Propylene Glycol | 5-25 |
| Tocopherol acetate | 0.2 |
| Water/Saline/Buffer | To 100 |

The composition was prepared by the methods described in previous examples. The nasal composition contains 10-120 mg/mL prednisolone.

The composition could be administered as drops, nebulation, spray, device, special device for nasal delivery to brain.

Doses in humans: The initial dosage of prednisolone may vary from 2 mg to 60 mg per day. The initial dosage should be maintained or adjusted until a satisfactory response is noted.

The nasal composition is administered from 1 to 4 times every day or every other day or once a week.

Example 44

Effect of GA and Prednisolone Innovative Formulation on Treatment of EAE

EAE was induced in Female C57Bl/6 mice 6-7 weeks old with body weight 16.84±1.23 g, according to protocol described in Example 37.
EAE Treatment with Nasal Compositions of the Invention Versus Controls:

Compositions were administered once daily, beginning on ~11$^{th}$ day (treatment was initiated when individual mice developed a clinical score EAE≥0.5) until the end of the study.

Four experimental groups were used, each containing 6 animals:

Group 1: Intranasal administration of prednisolone composition (Example 38) at a dose of 5.7 mg/Kg animal (0.1 mg/20 μl/mouse). 10 1 of the Composition were administered in each nostril once daily.

Group 2: Intranasal administration of GA composition (Example 39) at a dose of 13.7 mg/Kg animal (240 mcg/20 μl/mouse). 10 μl of the Composition were administered in each nostril once daily.

Group 3: Subcutaneous administration of GA control solution (Example 40) at a dose of 13.7 mg/kg. 200 μl of the solution were administered once a day to the mice (240 μg GA/animal/day).

Group 4: Control: no treatment.

FIG. 18 is a plot presenting the results obtained in this experiment. The results show that intranasal administration of GA and Prednisolone from the Compositions of the invention (Examples 38 and 39, respectively) efficiently treated EAE (a model of Multiple Sclerosis). For example, from day 22 to the end of the experiment the following EAE scores were obtained at the plateau:

Group 1 (Intranasal prednisolone novel composition) ~0.4
Group 2 (Intranasal GA novel composition) ~from 0.5 to 0
Group 3 (Subcutaneous GA control solution) ~1.5
Group 4 (Untreated control) ~3

Example 45

Effect of Intranasal GA Aqueous Control Solution on EAE in Mice

EAE was induced in Female C57Bl/6 mice 6-7 weeks old, according to protocol described in Example 37.
Treatment:

This experiment was carried out to test if nasal administration of GA solution not in the carrier of the invention is effective in EAE model.

Compositions were administered once daily, beginning on ~11$^{th}$ day (treatment was initiated when individual mice developed a clinical score EAE≥0.5) until the end of the study.

The following experimental groups were used, each containing 6 animals:

Group 1: Intranasal administration of GA aqueous control (Example 41) at a high dose of 13.7 mg/Kg animal (240 mcg/20 μl/mouse). 10 μl of the Composition were administered in each nostril once daily.

Group 2: Control: no treatment.

FIG. 19 is a graph presenting the results obtained in this experiment. The results show that intranasal administration of GA from aqueous solution had no effect on EAE (a model of Multiple Sclerosis) and were not different from untreated mice.

Example 46

Effect of Treatment of EAE in Mice with Low Dose GA in Nasal Compositions of the Invention Treatment:

Compositions were administered once daily, beginning on ~11$^{th}$ day (treatment was initiated when individual mice developed a clinical score EAE≥0.5) until the end of the study.

EAE was induced in Female C57Bl/6 mice, according to protocol described in Example 37.

Three experimental groups were used, each containing 6 animals:

Group 1: Intranasal administration of GA composition (Example 39) at a dose of 6:85 mg/Kg animal (120 mcg/10 μl/mouse). Composition was administered once daily.

Group 2: Subcutaneous administration of GA control solution (Example 40) at a dose of 6.85 mg/kg. 100 μl of the solution were administered once a day to the mice (120 μg GA/animal/day).

Group 3: Control: no treatment.

The results presented in FIG. 20 show that intranasal administration of a low dose of GA from the Compositions of the invention (Example 39) efficiently treated EAE (a model of Multiple Sclerosis) as compared to SC administration of the same drug dose. Scores at day 22 of the experiment were:

| Group | Treatment | Score at day 22 | Score at day 22 to day 26 (experiment end) |
|---|---|---|---|
| 1 | Intranasal GA novel composition | 2 | 2-1.8 |
| 2 | Subcutaneous GA control solution | 3.8 | 3.8-3.2 |
| 3 | Untreated control | 4 | 4-3.1 |

These results indicate that it is possible to reduce drug dose by administration of the drug in nasal Compositions of the invention.

Combination of at Least Two Active Ingredients

As indicated above the present invention concerns in general specific pharmaceutical compositions having a combination of at least two active ingredients.

Preferably the pharmaceutical compositions are administered intranasally. Among the advantages of the nasal administration of a combination of two or more drugs, in the compositions of the invention are:

By using a combination of drugs within the compositions for nasal administration, they could offer efficient treatment by using lower doses of the drugs than those needed without the compositions of the invention. For drugs with serious side effects this is an important advantage.

The combination of the two or more drugs are administrated as a single unit, improving patient compliance.

The combination of the two or more drugs show enhanced efficiency versus a single drug administration.

Pain Treatment with Intranasal Administration of Diazepam and Diclofenac Mixture Composition Example 47

Diazepam (Lower Dose) and Diclofenac Amalgam Nasal Composition

| Component, % w/w | |
|---|---|
| diazepam | 0.3125 |
| Diclofenac Sodium | 1.25 |
| Phospholipid | 2 |
| Ethanol | 15 |
| Propylene Glycol | 22 |
| Vitamin E | 0.2 |
| Distilled Water | To 100 |

The above formulation was prepared as follows: phospholipid was dissolved in ethanol and propylene glycol was added to this solution followed by addition of Vitamin E and mixing. Then, Diazepam was added to this mixture followed by addition of diclofenac sodium and stirring for another 10 minutes. Water was added slowly with constant stirring by a Heidolph overhead stirrer. The composition is stirred for additional 15 minutes. The final composition contains 6.25 mg/mL Diazepam.

Example 47A

Diazepam and Diclofenac Amalgam Nasal Composition

| Component, % w/w | |
|---|---|
| Diazepam | 1 |
| Diclofenac Sodium | 7.5 |
| Phospholipid | 2.5 |
| Ethanol | 16 |
| Propylene Glycol | 25 |
| Vitamin E | 0.2 |
| Buffer | To 100 |

Example 48

Composition Containing Opiates and Anti-Inflammatory Agents

| Component, % w/w | |
|---|---|
| Fentanyl | 0.01-1 |
| Diclofenac Sodium | 0.5-10 |
| Phospholipid | 3 |
| Ethanol | 17 |
| Propylene Glycol | 17 |
| Vitamin E | 0.2 |
| Distilled Water | To 100 |

Suggested dose of Fentanyl is in the range of 10-300 mcg per each administration. Suggested dose of diclofenac 0.05-100 mg per each administration.

Example 49

Test of Analgesic Effect of Diazepam and Diclofenac Nasal Compositions in Mice

The analgesic efficacy of the intranasal administration of the diclofenac-diazepam and diazepam containing composition (compositions detailed in Examples 47, 28-29, respectively) was tested.

The experiments were carried out on female C75/BL mice (8-9 weeks).

The following experimental groups of 4 animals, each, were used:

Group 1: Intranasal administration of Diazepam low dose composition as given in Example 29.

Group 2: Intranasal administration of Diazepam high dose composition as given in Example 28.

Group 3: Intranasal administration of Diazepam and Diclofenac composition containing a low dose of Diazepam and Diclofenac as given in Example 47.

The results were compared to the untreated control animals.

Intraperitoneal injection of a weak solution of acetic acid induces a nociceptive stereotyped behavior (writhing) that mimics acute pain. This model is widely used to evaluate the analgesic (antinociceptive) effects of anti pain drugs.

The mice received treatment under Isoflurane® anesthesia. Half an hour after the treatment, all the mice in the 3 groups were intraperitoneally administered with acetic acid 0.6% (10 ml/kg) and individually housed in cages with a smooth flat floor.

Antinociception effect was recorded by counting the number of writhes 5 minutes after the injection of acetic acid for a period of 10 minutes. A writhe is indicated by abdominal constriction and stretching of at least one hind limb.

From results presented in FIG. 21 it is obvious that administration of the nasal composition of Diclofenac and Diazepam, as given in Example 47, totally diminished the pain induced by injection of acetic acid solution. The composition has much higher effect than Diazepam administered at the same low dose and even Diazepam administered at a twice higher dose. The implication of these results could be in reducing the drug doses when using the combined composition.

Multiple Sclerosis Treatment with Intranasal Administration of Glatiramer Acetate (GA) and Cannabidiol (CBD) Mixture Compositions Example 50

Nasal Composition of the Invention Containing Glatiramer Acetate (GA)

| Component, % w/w | |
| --- | --- |
| Phospholipid | 5 |
| Ethanol | 15 |
| Propylene Glycol | 20 |
| Vitamin E | 0.2 |
| GA aqueous solution for injection | To 100 |

10 grams of the above formulation were prepared as follows: 0.5 g soy phospholipid was dissolved in 1.5 g ethanol and 2 g propylene glycol was added to this solution followed by addition of Vitamin E and mixing for 5 minutes. Then, GA aqueous solution containing 20 mg/mL GA was added slowly with constant stirring by a Heidolph overhead stirrer. The composition is stirred for additional 15 minutes. The final composition contains 12 mg/mL GA.

Example 51

GA Solution for Subcutaneous (SC) Administration

Control Solution

| | |
| --- | --- |
| Copaxone ® injection (20 mg/mL) | 180 µl |
| Normal saline to | 3000 µl |

Example 52

Nasal Composition of the Invention Containing GA and CBD (Cannabidiol)

| Component, % w/w | |
| --- | --- |
| CBD | 4 |
| Phospholipid | 5 |
| Ethanol | 15 |
| Propylene Glycol | 20 |
| Vitamin E | 0.2 |
| GA aqueous solution for injection | To 100 |

The composition was prepared by the methods described above.

The final composition contains 11.2 mg/mL GA and 40 mg/mL CDB.

Example 52A

Nasal Composition of the Invention Containing GA and CBD

| Component, % w/w | |
| --- | --- |
| CBD | 2 |
| Phospholipid | 5 |
| Ethanol | 15 |
| Propylene Glycol | 20 |
| Vitamin E | 0.2 |
| GA aqueous solution for injection | To 100 |

The composition was prepared by the methods described above.

The final composition contains 11.2 mg/mL GA and 20 mg/mL CDB.

Example 53

Nasal Composition of the Invention Containing GA and CBD

| Component, % w/w | |
| --- | --- |
| CBD | 1.2 |
| Phospholipid | 5 |
| Ethanol | 15 |
| Propylene Glycol | 20 |
| Vitamin E | 0.2 |
| GA aqueous solution for injection | To 100 |

The final composition contains 11.8 mg/mL GA and 12 mg/mL CDB.

Example 54

Nasal Composition of the Invention Containing GA and CBD

| Component, % w/w | |
|---|---|
| GA | 0.5-12 |
| CBD | 0.1-10 |
| Phospholipid | 0.2-10 |
| Ethanol | 12-18 |
| Propylene Glycol | 0-25 |
| Tocopherol acetate or BHT | 0.02-0.5 |
| Water/Saline/Buffer | To 100 |

The composition was prepared by the methods described in previous examples. CBD is mixed/dissolved in Phospholipid/Ethanol/Propylene glycol phase. GA is added as an aqueous solution.

The GA solution could contain buffers, glycols, polyglycols, solubilyzers such as citrate esters, carbohydrates, mannitol, sugar alcohols, salts, stabilizers, antioxidants (BHA, BHT, sulfides, tocopherols, ascorbic acid derivatives).

The nasal composition contains 5-100 mg/mL GA and 1-100 mg/mL CBD.

The compositions could be administered as drops, nebulation, spray, device, special device for nasal delivery to brain.

Dosage of GA in humans: 0.5-80 mg GA administered as needed.

Dosage of CBD: 0.1-500 mg administered as needed.

Administration of the nasal composition could be made every day or every other day or once a week.

Example 55

Treatment of Experimental Allergic Encephalomyelitis (EAE) by Means of Intranasal GA-CBD Combination Evidence of Neurons Regeneration EAE in mice is an accepted model of Multiple Sclerosis in humans.
Induction of EAE:
EAE was induced in female C57Bl/6 mice, 6-7 weeks old (weighting 17-18 g) using a slightly modified previously published protocol [Kataoka H, et al. Cell Mol. Immunol. 2005]. By using this procedure, the mice were immunized with Myelinoligodendrocyte glycoprotein ($MOG_{35-55}$) peptide mixed with mycobacteria in Complete Freund's adjuvant (CFA), followed by immediate and 48 hours later injections of Pertussis toxin.

Clinical assessment is performed on the basis of the EAE score scale (see Example 37 for details).

The following experimental groups were used, each containing 6 animals:

Compositions were administered to mice in all treatment groups once daily, beginning on ~$11^{th}$ day (treatment was initiated when individual mice developed a clinical score EAE≥0.5) until the end of the study.

Four experimental groups were used:
Group 1: Intranasal administration of GA-CBD composition.

Composition of Example 52 at a dose of 6.8 mg GA/Kg animal and 24.45 mg CBD/Kg animal (10 μl/mouse) was administered for the first 3 days from the development of EAE.

Further, until the end of the experiment, composition of Example 52A at a dose of 6.8 mg GA/Kg animal and 12.2 mg CBD/Kg animal (10 μl/mouse) was administered Composition was administered once daily.

Two mice were injected intraperitoneally daily from day 20 to end of experiment 50 mg/Kg BrDU (5-Br-2'-deoxyuridine), a thymidine analog that incorporates into the DNA of dividing brain neurons.

At the end of the experiment, the mice were sacrificed, the brain was removed for neurogenesis analysis.

Group 2: Intranasal administration of GA composition (Example 50) at a GA dose of 6.8 mg/Kg animal (120 mcg/10 μl/mouse). Composition was administered once daily.

Group 3: Subcutaneous administration of GA control solution (Example 51) at a GA dose of 6.8 mg/kg.

100 μl of the solution were administered once a day to the mice (120 μg GA/animal/day).

Group 4: Control—no treatment.

Two mice were injected intraperitoneally daily from day 20 to end of experiment 50 mg/Kg BrDU (5-Br-2'-deoxyuridine), a thymidine analog that incorporates into the DNA of dividing brain neurons.

At the end of the experiment, the mice were sacrificed, the brain was removed for neurogenesis analysis.

The results presented in FIG. 22 show that intranasal administration of the combination composition containing a low dose GA and CBD was much more efficient in treating EAE in mice than intranasal administration of the same dose GA alone or the same dose of GA administrated subcutaneously.

At the end of the experiment (day 26) the following EAE scores were obtained:
Group 1 (Intranasal GA-CBD compositions) ~0.5
Group 2 (Intranasal GA composition) ~2
Group 3 (Subcutaneous GA control solution) ~3.4
Group 4 (Untreated control) ~3

Hystological sections show a high regeneration of active neurons only on mice treated intranasally with GA-CBD (from group 1).

Example 56

Effect of Intranasal Treatment with GA-CBD Composition on EAE in Mice

Regeneration in Untreated Control Animals and Animals Administrated with GA Aqueous Solution Treatment:
This experiment is a continuation of the experiment described in Example 45. Starting from day 16 after EAE induction, animals were re-divided into four new groups according to the following treatment schedule scheme.

Group 1A: Two mice from the group previously treated with intranasal GA aqueous solution now were treated intranasally with composition of Example 53.

Group 1B: Two mice from the group previously treated with intranasal GA aqueous solution now were untreated.

Group 2A: Three previously untreated mice—remained untreated.

Group 2B: One previously untreated mouse now was treated intranasally with composition of Example 53.

Table VI presents the results of experiment in Example 56. The results show the reduction in EAE scores when the mice from day 16 where treated with the combination of GA and CBD, pointing toward regeneration of the condition. In Group 1A, on day 22 the mean score was 2 showing a reduction of 1 score (from 3 to 2) and in Group 2B the reduction was by 2 scores, from score 4 to score 2. In both untreated mice groups, 1B and 2A, the scores remained essentially the same.

TABLE VI

| | Mean scores | | | |
|---|---|---|---|---|
| Day | Group 1A | Group 1B | Group 2A | Group 2B |
| 16 | 3 | 3 | 3.5 | 4 |
| 17 | 2.5 | 3 | 4 | 2 |
| 18 | 2 | 3.35 | 4 | 2 |
| 19 | 2.5 | 3.8 | 4 | 2 |
| 20 | 3 | 3 | 3.65 | 2 |
| 21 | 2 | 3 | 3.65 | 2 |
| 22 | 2 | 3 | 3.65 | 2 |

Example 57

Effect of Apomorphine Administered Nasally in Parkinson Model Rats

Experiments were carried out on adult male SD/H rats weighing 175-225 grams obtained from the institute animal facility.

For the stereotaxic surgery, rats have been anaesthetized by mixture of Ketamine: Xylazine 85:15 in dose of 0.1 ml/100 grams intraperitoneally Animals were then positioned in a stereotaxic frame in flat skull position. The flat skull position was achieved when the incisor bar was lowered to 3.5 mm below the horizontal zero. A 2 centimeter midsagittal incision was made in the scalp with sterile blade, the skin and inferior tissue layers covering the skull were retracted and a small hole was drilled at the following coordinates: lateral (L) +1.2; antero-posterior (AP) −4.3, ventral (V) −8.3 from the bregma point.

6-OHDA with 0.2% ascorbic acid (8 μg in 4 μl in saline) was infused {at rate of 1 μl/minute for 4 minutes (automatic Hamilton syringe (KD Scientific) and left in place for another 5 minutes and then was withdrawn unilaterally through a 30-gauge stainless steel cannula stereotaxically placed via a the hole of the skull and advanced so that the internalized tip was located within the nigrostriatal pathway. Animals were allowed to recover completely before being returned to housing.

Two weeks post-lesioning, rats were injected (s.c.) with apomorphine hydrochloride-APO-(0.20 mg/kg) individual animals will be placed in a rotometer and contra-lateral rotations were counted. More than 6 rotations/minute were considered positive for successful lesion.

The following compositions were prepared:

| Composition | % w/w |
|---|---|
| Formulation A | |
| Apomorphine hydrochloride hemihydrate | 0.05 |
| Ethanol | 13 |
| Propylene glycol | 20 |
| Phospholipon 90 G | 5 |
| Vitamin E acetate | 0.2 |
| Distilled Water | to 100 |
| Formulation B | |
| Apomorphine hydrochloride hemihydrate | 0.05 |
| Vitamin E acetate | 0.2 |
| Distilled water | 99.75 |
| Formulation C | |
| Apomorphine hydrochloride hemihydrate | 0.005 |
| Distilled Water to | 100 |

Animals with successful lesions were divided randomly into three groups. Apomorphine was administrated nasally or subcutaneously in doses of 0.05 mg/Kg to these rats and the stereotypic contra-lateral rotations were counted.

Group A—Intranasal—Apomorphine hydrochloride hemihydrate—Formulation A: 4 rats received each 0.05 mg/Kg Apomorphine hydrochloride hemihydrate as 30 microliters formulation A. After a 4-minute waiting period, individual animals were placed in a rotometer and contra-lateral rotations were counted.

Group B—Intranasal—Apomorphine hydrochloride hemihydrate—Formulation B: 4 rats received each 0.05 mg/Kg Apomorphine hydrochloride hemihydrate as 30 microliters formulation B. After a 4-minute waiting period, individual animals were placed in a rotometer and contra-lateral rotations were counted.

Group C—Subcutaneous—Apomorphine hydrochloride hemihydrate—Formulation C: 4 rats received each 0.05 mg/Kg Apomorphine hydrochloride hemihydrate as 30 microliters formulation C. After a 4-minute waiting period, individual animals were placed in a rotometer and contralateral rotations were counted.

Results:

| Animals | Administration route | Formulation | Dose | Response | Mean Retaliation per minute |
|---|---|---|---|---|---|
| A - Intranasal - Apomorphine hydrochloride hemihydrate - Formulation A | | | | | |
| 1 | nasal | Formulation A | 0.05 mg/Kg | yes | 21 |
| 2 | nasal | Formulation A | 0.05 mg/Kg | yes | 15 |
| 3 | nasal | Formulation A | 0.05 mg/Kg | No | 0 |
| 4 | nasal | Formulation A | 0.05 mg/Kg | yes | 19 |
| | | | Mean | 75% response | 13.75 |
| | | | SEM | | 4.6 |
| B - Intranasal - Apomorphine hydrochloride hemihydrate - Formulation B | | | | | |
| 1 | nasal | Formulation B | 0.05 mg/Kg | yes | 10 |
| 2 | nasal | Formulation B | 0.05 mg/Kg | yes | 5 |

-continued

| Animals | Administration route | Formulation | Dose | Response | Mean Retaliation per minute |
|---|---|---|---|---|---|
| 3 | nasal | Formulation B | 0.05 mg/Kg | No | 0 |
| 4 | nasal | Formulation B | 0.05 mg/Kg | No | 0 |
| | | | Mean | 50% response | 3.75 |
| | | | SEM | | 2.2 |
| C - Subcutaneous - Apomorphine hydrochloride hemihydrate - Formulation C | | | | | |
| 1 | subcutaneous | Formulation C | 0.05 mg/Kg | yes | 17 |
| 2 | subcutaneous | Formulation C | 0.05 mg/Kg | yes | 12 |
| 3 | subcutaneous | Formulation C | 0.05 mg/Kg | yes | 12 |
| 4 | subcutaneous | Formulation C | 0.05 mg/Kg | yes | 18 |
| | | | Mean | 100% response | 14.75 |
| | | | SEM | | 1.6 |

The results presented herein and in FIG. 23 show that the effect of Nasal administration of apomorphine in the carrier of the invention in Parkinson model rats was equivalent to the effect of subcutan administration. Almost no effect was obtained with nasal administration of formulation B containing apomorphine aqueous solution.

Example 58

Therapeutic Efficacy of Dexamethasone (DEX) Administrated Nasally from the Formulation of the Invention in EAE Mice Model Experiments were conducted on female C57Bl/6 mice, 6-7 weeks old. Each mouse was weight every day during study time.

Mice were immunized with 300 μg of $MOG_{35-55}$ peptide mixed with 0.1 ml (5 mg mycobacteria) in Complete Freund's adjuvant (CFA). A volume of 0.2 ml of the mixture was injected at the base of the tail for each mouse. Pertussis toxin (200 ng/mouse) was injected immediately and 48 hours later in volume of 0.1 ml. Clinical assessment was performed on the basis of the EAE score (presented in Example 37 above).

The following formulations were prepared:

| Composition | % w/w |
|---|---|
| Formulation A | |
| Dexamethasone 21 Sodium Phosphate aqueous solution for injection | 34 |
| Ethanol | 15 |
| Propylene glycol | 20 |
| Phospholipon 90 G | 5 |
| Vitamin E acetate | 0.2 |
| Distilled water | 25.8 |
| Formulation B | |
| Dexamethasone 21 Sodium Phosphate aqueous solution for injection | 34 |
| Vitamin E acetate | 0.2 |
| Formulation C | |
| Distilled water | 65.8 |
| Dexamethasone 21 | 0.34 |

-continued

| Composition | % w/w |
|---|---|
| Sodium Phosphate aqueous solution for injection | |
| Distilled Water to | 100 |

The final composition contains 5.25 mg/mL DEX*
*1.3 mg of Dexamethasone sodium phosphate is equivalent to 1 mg of Dexamethasone Animals were divided into experimental groups, as follows:

Group A—Intranasal—Dexamethasone 21 sodium Phosphate 1—Formulation A: 7 mice received each 3 mg/Kg Dexamethasone 21 sodium Phosphate as 10 microliters formulation A once a day. Treatment was initiated when individual mice developed a clinical score EAE≥0.5 until the end of the study.

Group B—Intranasal—Dexamethasone 21 sodium Phosphate 1—Formulation B: 7 mice received each 3 mg/Kg Dexamethasone 21 sodium Phosphate as 10 microliters formulation B once a day. Treatment was initiated when individual mice developed a clinical score EAE≥0.5 until the end of the study.

Group C—Oral—Dexamethasone 21 sodium Phosphate 1—Formulation C: 7 mice received each 3 mg/Kg Dexamethasone 21 Sodium Phosphate as 100 microliters formulation C once a day. Treatment was initiated when individual mice developed a clinical score EAE≥0.5 until the end of the study.

Group D—Control: no treatment.

Results in FIG. 24 indicate that administration of DEX in the formulation of the invention enabled statistical significant reduction in EAE scores, versus control ill mice and versus nasal aqueous solution Example 59

Analgesic Effects of Tramadol in Nasal Formulations in Pain Model Mice

Experiments were conducted on male ICR mice (35 grams, n=6). Antinociception was recorded by counting the number of writhes 5 minutes after injection of acetic acid for a period of 10 minutes. A writhe is indicated by abdominal constriction and stretching of at least one hind limb. In this test, the intraperitoneally injection of a weak solution of acetic acid induces a nociceptive stereotyped behavior (writhing) that mimics acute visceral pain. The model has been validated in rats and mice and is widely used to evaluate the antinociceptive effects of opioid and non-opioid analgesics (Collier et al., 1968). Tramadol (10 mg/kg) in total was nasally administered to each mouse (under anesthesia with Isoflurane®) 6 and 3 hours before Acetic Acid solution 0.6% (10 ml/kg) administration.

The following formulation was prepared:

| Composition | % w/w |
| --- | --- |
| Tramadol HCl | 0.9 |
| Ethanol | 14 |
| Propylene glycol | 20 |
| Phospholipon 90 G | 5 |
| Vitamin E acetate | 0.2 |
| Distilled Water to | 100 |

Experimental groups were prepared as follows:

Group A: 3 mice each intranasally received 10 mg/Kg of the Tramadol HCl (18 microliters) formulation described herein.

Group B—3 mice were untreated and used as a control.

FIG. 25 presents the results of a writhing test in mice following nasal administration of tramadol HCl (drug dose 5 mg/kg, A) versus untreated control (B) and shows that a statistically significant antinociceptive (analgesic) effect (P<0.001 Formulation A vs. control) was obtained when Tramadol formulation was administered (6 hours—5 mg/Kg and 3 hours 5 mg/Kg) before Acetic Acid injection. This shows that the nasal administration of our tramadol composition has a prolonged analgesic effect.

Example 60

Analgesic Effects of Tramadol in the Nasal Formulations in Pain Model Mice

Experiments were conducted on male C57Bl/6 mice (8-9 weeks). Antinociception was recorded by counting the number of writhes 5 minutes after injection of acetic acid for period of 10 minutes. A writhe is indicated by abdominal constriction and stretching of at least one hind limb. In this test, the intraperitoneally injection of a weak solution of acetic acid induces a nociceptive stereotyped behavior (writhing) that mimics acute visceral pain. The model has been validated in rats and mice and is widely used to evaluate the antinociceptive effects of opioid and non-opioid analgesics (Collier et al., 1968).

Tramadol (5 mg/kg) was delivered to each mouse under anesthesia with Isoflurane®, immediately before Acetic Acid solution 0.6% (10 ml/kg) administration.

The following formulations were prepared:

| Formulation A | |
| --- | --- |
| Composition | % w/w |
| Tramadol HCl | 0.9 |
| Ethanol | 15 |
| Propylene glycol | 20 |
| Phospholipon 90 G | 5 |
| Vitamin E acetate | 0.2 |
| Distilled water | 58.9 |

The final composition contains 9 mg/mL Tramadol HCl.

| Formulation B | |
| --- | --- |
| Composition | % w/w |
| Tramadol HCl | 0.09 |
| Distilled water | 99.91 |

Experimental groups were devised as follows:

Group A—Intranasal—Tramadol HCl—Formulation A.

6 mice received each 5 mg/Kg Tramadol as 12 microliters formulation A

Group B—Oral—Tramadol HCl—Formulation B.

6 mice received each 5 mg/Kg Tramadol as 120 microliters formulation B

Group C—Control—untreated mice.

FIG. 26 presents the results of a writhing test in mice following nasal administration of tramadol HCl (drug dose 5 mg/kg, A) versus aqueous solution (B) and untreated control (C) and shows that a significant antinociceptive (analgesic) effect (*P<0.001 formulation A vs. Formulation B and control) was obtained only by nasal administration of the drug in our formulation.

Example 61

Therapeutic Effect of Glatiramer Acetate (GA) Administrated Nasally from the Innovative Nasal Delivery Carrier in EAE Mice Model Experiments were conducted on Female C57Bl/6 mice, 6-7 weeks old. Mice were immunized with 300 μg of $MOG_{35-55}$ peptide mixed with 0.1 ml (5 mg mycobacterium) in Complete Freund's adjuvant (CFA). A volume of 0.2 ml of the mixture was injected at the base of the tail for each mouse. Pertussis toxin (200 ng/mouse) was injected immediately and 48 hours later in volume of 0.1 ml. Clinical assessment was performed on the basis of the following scale (EAE score, see Example 37).

The following formulations were prepared:

| Composition | % w/w |
| --- | --- |
| Formulation A | |
| GA aqueous solution for injection | 59.8 |
| Ethanol | 14 |
| Propylene glycol | 15 |
| Phospholipon 90 G | 3 |
| Tocopherol | 0.2 |
| Water | 8.0 |
| Formulation B | |
| GA aqueous sol. for injection | 59.8 |
| Tocopherol | 0.2 |
| Water to | 100 |
| Formulation C | |
| GA aqueous sol. for injection | 24.0 |
| Water to | 100 |

The final composition contains 12 mg/mL GA

Each group contained 7 animals, as follows:

Group A—Intranasal—Glatiramer acetate1 of Formulation A: 7 mice received each 13.7 mg/Kg Glatiramer acetate as 20 microliters formulation A once a day. Treatment was initiated when individual mice developed a clinical score EAE≥0.5 until the end of the study.

Group B—Intranasal—Glatiramer acetate—Formulation B: 7 mice received each 13.7 mg/Kg Glatiramer acetate as 20 microliters formulation B once a day. Treatment was initiated when individual mice developed a clinical score EAE≥0.5 until the end of the study.

Group C—Subcutaneous—Glatiramer acetate—Formulation C: 7 mice received each 13.7 mg/Kg Glatiramer acetate as 50 microliters formulation C once a day, treatment was initiated when individual mice developed a clinical score EAE≥0.5 until the end of the study.

Group D—Control: no treatment.

FIG. 27 presents a statistically significant therapeutic effect was obtained in ill mice when formulation A was administered nasally (versus formulation B and versus Control).

Example 62

Therapeutic Efficacy of a New Drug Combination Glatiramer Acetate and Cannabidiol (GA & CBD) Administrated Nasally and Subcutaneous in EAE Mice Model Experiments were conducted on female C57Bl/6 mice, 6-7 weeks old.

Mice were immunized with 300 μg of $MOG_{35-55}$ peptide mixed with 0.1 ml (5 mg mycobacterium) in Complete Freund's adjuvant (CFA). A volume of 0.2 ml of the mixture was injected at the base of the tail for each mouse. Pertussis toxin (200 ng/mouse) was injected immediately and 48 hours later in volume of 0.1 ml. Clinical assessment was performed on the basis of the following scale (EAE score, see Example 37).

The following formulations were prepared:

| Formulation A | |
|---|---|
| Composition | % w/w |
| GA aqueous solution | 58.6 |
| CBD | 1.2 |
| Ethanol | 15 |
| Propylene glycol | 21 |
| Phospholipon 90 G | 4 |
| Vitamin E acetate | 0.2 |

The composition is stirred for additional 15 minutes. The final composition contains 12 mg/mL GA and 12 mg/ml CBD.

| Formulation B | |
|---|---|
| Composition | % w/w |
| GA aqueous sol. For injection | 12 |
| CBD | 0.24 |
| Ethanol | 15 |
| Propylene glycol | 21 |
| Phospholipon 90 G | 4 |
| Vitamin E acetate | 0.2 |
| Distilled water | 47.6 |

The final composition contains 2.4 mg/mL GA and 2.4 mg/ml CBD.

Experimental groups were prepared as follows, each group containing 5 animals:

Group A—Intranasal—Glatiramer acetate and CBD—Formulation A: 5 mice received each, the combination (GA & CBD Glatiramer acetate 6.8 mg/kg and CBD 6.7 mg/kg) as 10 microliters formulation A once a day. Treatment was initiated when individual mice developed a clinical score EAE≥0.5 until the end of the study.

Group B—Subcutaneous—Glatiramer acetate and CBD—Formulation B: 5 mice received each, the combination (GA & CBD Glatiramer acetate 6.8 mg/kg and CBD 6.7 mg/kg) as 50 microliters formulation B once a day. Treatment was initiated when individual mice developed a clinical score EAE≥0.5 until the end of the study.

Group C. Control: no treatment: Untreated mice.

Results:

| Group | Incidence | Mortality | Mean (±SE) Duration (days) | Mean (±SE) Onset (days) | Mean (±SE) Group Score | Mean (±SE) Maximal Score |
|---|---|---|---|---|---|---|
| Formulation A IN-GA/CBD Therapeutic 6.7 mg/6.7 mg/kg | 5/5 | 0 | 16 ± 1.79 | 14 ± 1.8 | 0.39 ± 0.29 | 1.2 ± 0.33 |
| Formulation B SC-GA/CBD Therapeutic 6.7 mg/6.7 mg/kg | 4/5 | 1 | 18.5 ± 0.87 | 11.5 ± 0.9 | 1.25 ± 0.48 | 2.25 ± 0.48 |
| C-No-treatment | 4/5 | 1 | 19 ± 1.78 | 11 ± 1.78 | 2.67 ± 0.62 | 4.5 ± 0.5 |

The above table and FIG. 28 presents clinical manifestations of EAE following intranasal administration of CBD and GA, following subcutaneous administration thereof versus untreated control and show that both the nasal administration and the subcutan administration of the drug combination were statistically significant efficient versus control ill mice in reducing the illness. *P<0.05 Formulation A vs. Control, **P<0.05 Formulation B vs. Control with the nasal administration being the most efficient treatment.

The invention claimed is:

1. A method for the systemic administration of at least one active pharmaceutical agent, other than a nucleic acid, to a mammal, which method comprises administering to the mucous membranes of the nasal passage or nasal cavity of a mammal in need of the systemic administration of said agent, a composition comprising a therapeutically effective amount of said agent, phospholipids, one or more C2-C4 alcohols and water, wherein the concentrations of said phospholipids and said one or more alcohols in said composition are in the ranges of 0.2 to 10% and 12 to 30% by weight, respectively, with the water content of said composition being not less than 30% by weight, said phospholipids forming vesicles in said composition.

2. The method according to claim 1, wherein said composition further includes one or more water-miscible polyols, wherein the concentration of said one or more polyols in said composition is in the range of 1 to 30% by weight.

3. The method according to claim 1, wherein the C2-C4 alcohol is ethanol.

4. The method according to claim 2, wherein the polyol is propylene glycol.

5. The method according to claim 1, wherein the weight ratio between said C2-C4 alcohol and said phospholipids is not less than 2:1.

6. The method according to claim 1, wherein said mammal is one in need of treatment of emesis, wherein said pharmaceutical agent is an anti-emetic agent.

7. The method of claim 6, wherein said anti-emetic agent is granisetron.

8. The method according to claim 1, wherein said mammal is one in need of treatment of diabetes, wherein said pharmaceutical agent is an anti-diabetic agent.

9. The method of claim 8, wherein said anti-diabetic agent is insulin or derivative thereof.

10. The method according to claim 1, wherein said mammal is one in need of treatment of malaria, wherein said pharmaceutical agent is an anti-malaria drug.

11. The method according to claim 1, wherein said mammal is one in need of treatment of epileptic seizures, wherein said pharmaceutical agent is an anti-epileptic agent.

12. The method of claim 11, wherein said anti-epileptic agent is diazepam.

13. The method according to claim 1, wherein said mammal is one in need of treatment of depression and/or anxiety, wherein said pharmaceutical agent is an anti-depressant agent.

14. The method of claim 13, wherein said anti-depressant agent is selected from group consisting of diazepam and buspirone hydrochloride.

15. The method according to claim 1, wherein said mammal is one in need of treatment of obesity, wherein said pharmaceutical agent is an anti-obesity agent.

16. The method of claim 15, wherein said anti-obesity agent is sibutramine.

17. The method according to claim 1, wherein said mammal is one in need of treatment of depression and/or hot flushes, wherein said pharmaceutical agent is an anti-depression agent/anti-hot flushes agent.

18. The method of claim 17, wherein said anti-depression/anti-hot flushes agent is paroxetine or a pharmaceutically acid addition salt thereof.

19. The method according to claim 1, wherein said mammal is one in need of treatment of multiple sclerosis, wherein said pharmaceutical agent is an anti-multiple sclerosis agent.

20. The method of claim 19, wherein said anti-multiple sclerosis agent is glatiramer acetate (GA).

21. The method according to claim 1, wherein said mammal is one in need of treatment of dementia, wherein said pharmaceutical agent is an anti-dementia agent.

22. The method of claim 21, wherein said dementia is Alzheimer disease.

23. The method of claim 22, wherein said anti-dementia agent is rivastigmine.

24. The method according to claim 1, wherein said mammal is one in need of treatment of pain, wherein said pharmaceutical agent is an analgesic agent.

25. The method of claim 24, wherein said analgesic agent is tramadol.

26. The method according to claim 1, wherein said mammal is one in need of induction of sleep, wherein said pharmaceutical agent is a hypnotic agent.

27. The method of claim 26, wherein said hypnotic agent is brotizolam or any pharmaceutically acceptable salt thereof.

28. The method of claim 27, wherein said hypnotic agent is diphenhydramine hydrochloride or any pharmaceutically acceptable salt thereof.

29. The method according to claim 1, wherein said mammal is one in need of treatment of an inflammatory associated disease or disorder, wherein said pharmaceutical agent is a corticosteroid agent.

30. The method of claim 29, wherein the inflammatory associated disease or disorder is an autoimmune disease.

31. The method of claim 30, wherein said autoimmune disease is multiple sclerosis.

32. The method of claim 29, wherein said corticosteroid agent is selected from the group consisting of dexamethasone and any pharmaceutically acceptable derivatives or salts thereof.

33. The method of claim 29, wherein said corticosteroid agent is selected from the group consisting of prednisolone and any pharmaceutically acceptable derivatives or salts thereof.

34. The method according to claim 1, wherein said mammal is one in need of treatment of Parkinson, wherein said pharmaceutical agent is an anti-parkinson agent.

35. The method of claim 34, wherein said anti-parkinson agent is apomorphine.

36. The method of claim 19, wherein said C2-C4 alcohol is ethanol.

37. The method of claim 24, wherein said C2-C4 alcohol is ethanol.

38. The method according to claim 1, wherein said mammal is one in need of treatment of multiple sclerosis, wherein said pharmaceutical agent is a combination of glatiramer acetate and cannabidiol.

39. The method according to claim 1, wherein said mammal is one in need of regeneration of neurons and/or cells in a brain of a mammal, wherein said pharmaceutical agent is a combination of glatiramer acetate and cannabidiol.

40. The method according to claim 1, wherein said mammal is one in need of treatment of pain, wherein said pharmaceutical agent is a combination of diazepam and diclofenac.

* * * * *